United States Patent
Shinoda et al.

(10) Patent No.: US 10,905,352 B2
(45) Date of Patent: Feb. 2, 2021

(54) MAGNETIC RESONANCE IMAGING APPARATUS AND MEDICAL IMAGE PROCESSING METHOD

(71) Applicant: TOSHIBA MEDICAL SYSTEMS CORPORATION, Otawara (JP)

(72) Inventors: Kensuke Shinoda, Sakura (JP); Takuya Fujimaki, Otawara (JP); Shuhei Nitta, Ohta (JP); Syuhei Takemoto, Niiza (JP); Shigehide Kuhara, Otawara (JP); Tomoyuki Takeguchi, Kawasaki (JP); Yurika Ogawa, Yokohama (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 561 days.

(21) Appl. No.: 14/948,661

(22) Filed: Nov. 23, 2015

(65) Prior Publication Data

US 2016/0155229 A1 Jun. 2, 2016

(30) Foreign Application Priority Data

Nov. 28, 2014 (JP) ................................ 2014-242507

(51) Int. Cl.
*G06K 9/00* (2006.01)
*A61B 5/055* (2006.01)
(Continued)

(52) U.S. Cl.
CPC ............ *A61B 5/055* (2013.01); *A61B 5/0044* (2013.01); *A61B 5/743* (2013.01); *G06T 19/00* (2013.01);
(Continued)

(58) Field of Classification Search
None
See application file for complete search history.

(56) References Cited

U.S. PATENT DOCUMENTS 6,381,296 B1 4/2002 Nishiura
7,280,862 B2 10/2007 Gupta et al.
(Continued)

FOREIGN PATENT DOCUMENTS

JP 2001-167251 A 6/2001
JP 2006-55641 A 3/2006
(Continued)

OTHER PUBLICATIONS

"CMR Image Acquisition Protocols" www.scmr.org, Version 1.0, Mar. 2007, 16 Pages.
(Continued)

*Primary Examiner* — Sean M Conner
(74) *Attorney, Agent, or Firm* — Oblon, McClelland, Maier & Neustadt, L.L.P.

(57) ABSTRACT

A magnetic resonance imaging apparatus according to embodiments includes processing circuitry. The processing circuitry configured to acquire layout information which defines a layout of cross-sectional images on a localizer screen, to detect cross-sectional positions of the cross-sectional images from MR data, and to generate the localizer screen according to the layout information, the localizer screen including all or a part of the plurality of cross-sectional images generated on the basis of the plurality of cross-sectional positions.

12 Claims, 16 Drawing Sheets

(51) Int. Cl.
  *A61B 5/00*   (2006.01)
  *G06T 19/00*  (2011.01)
  *G16H 30/40*  (2018.01)
  *G16H 50/50*  (2018.01)
  *A61B 5/026*  (2006.01)

(52) U.S. Cl.
  CPC ............. *G16H 30/40* (2018.01); *G16H 50/50* (2018.01); *A61B 5/0263* (2013.01); *A61B 2576/023* (2013.01); *G06T 2200/24* (2013.01); *G06T 2210/41* (2013.01); *G06T 2219/028* (2013.01)

(56) References Cited

U.S. PATENT DOCUMENTS

| | | | |
|---|---|---|---|
| 9,098,927 B2 | 8/2015 | Nitta et al. | |
| 2004/0109008 A1* | 6/2004 | Sako | G06T 7/0012 345/629 |
| 2011/0313291 A1* | 12/2011 | Chono | A61B 8/0883 600/440 |
| 2012/0126812 A1 | 5/2012 | Nitta et al. | |
| 2013/0129198 A1* | 5/2013 | Sherman | G06F 19/321 382/159 |
| 2015/0317434 A1* | 11/2015 | Kondo | A61B 5/00 705/3 |
| 2016/0047872 A1* | 2/2016 | Park | G01R 33/4818 324/309 |

FOREIGN PATENT DOCUMENTS

| | | |
|---|---|---|
| JP | 2012-110689 A | 6/2012 |
| JP | 5323194 B2 | 10/2013 |
| JP | 2014-121596 A | 7/2014 |
| WO | WO 2011/021254 A1 | 2/2011 |
| WO | WO 2013/027540 A1 | 2/2013 |

OTHER PUBLICATIONS

Office Action dated Jun. 26, 2018 in Japanese Patent Application No. 2014-242507.
Japanese Office Action dated Mar. 3, 2020 in corresponding Japanese Patent Application No. 2019-073440, 4 pages.

* cited by examiner

MAGNETIC RESONANCE IMAGING APPARATUS AND MEDICAL IMAGE PROCESSING METHOD

CROSS-REFERENCE TO RELATED APPLICATIONS

This application is based upon and claims the benefit of priority from Japanese Patent Application No. 2014-242507, filed on Nov. 28, 2014; the entire contents of which are incorporated herein by reference.

FIELD

Embodiments described herein relate generally to a magnetic resonance imaging apparatus.

BACKGROUND

Magnetic Resonance Imaging implements an imaging method by which atomic nucleus spins of an examined subject placed in a magnetostatic field are magnetically excited by a Radio Frequency (RF) pulse at a Larmor Frequency, so that an image is reconstructed from Nuclear Magnetic Resonance (NMR) signals that occur due to the excitation.

For example, standardized protocols are defined for methods for examining the heart through an MRI process. For instance, a standardized protocol defines a flow and the like in which a body axis transversal cross-sectional (axial) image, a sagittal cross-sectional image, and a coronal cross-sectional image that are called scout images or locator images are acquired, before acquiring multi-slice images represented by a plurality of body axis transversal cross-sectional (axial multi-slice) images are acquired, and subsequently reference cross-sectional images are acquired.

The reference cross-sectional images are cross-sectional images based on anatomical characteristics of the heart and include one or more of the following: left ventricular vertical long-axis images, left ventricular horizontal long-axis images, left (right) ventricular short-axis images, left (right) ventricular two-chamber long-axis images, (right) ventricular three-chamber long-axis images, left (right) ventricular four-chamber long-axis images, left (right) ventricular outflow tract images, aorta valve image and pulmonary valve images. Methods for setting reference cross-sectional images are also defined for other various imaged targets such as the brain, the shoulders, the knees, and the like.

DETAILED DESCRIPTION

A magnetic resonance imaging apparatus according to an aspect of the embodiments includes processing circuitry. The processing circuitry configured to acquire layout information which defines a layout of cross-sectional images on a localizer screen, to detect cross-sectional positions of the cross-sectional images from MR data, and to generate the localizer screen according to the layout information, the localizer screen including all or a part of the plurality of cross-sectional images generated on the basis of the plurality of cross-sectional positions.

A magnetic resonance imaging apparatus according to another aspect of the embodiments includes an MRI system, a processor, and a memory. An MRI system is configured to acquire an MR image. A memory sores processor-executable instructions. The processor-executable instructions, when executed by the processor, cause the processor to acquire layout information which defines a layout of cross-sectional images on a localizer screen, to detect cross-sectional positions of the cross-sectional images from MR data, and to generate the localizer screen according to the layout information. The localizer screen includes all or a part of the plurality of cross-sectional images generated on a basis of the plurality of cross-sectional positions.

Exemplary embodiments of a Magnetic Resonance Imaging apparatus (hereinafter, "MRI apparatus", as appropriate) will be explained below, with reference to the accompanying drawings. Possible embodiments are not limited to the embodiments described below. Further, the contents of each of the exemplary embodiments and the modification examples are, in principle, similarly applicable to any other embodiments and modification examples.

First Embodiment

Figure 1:
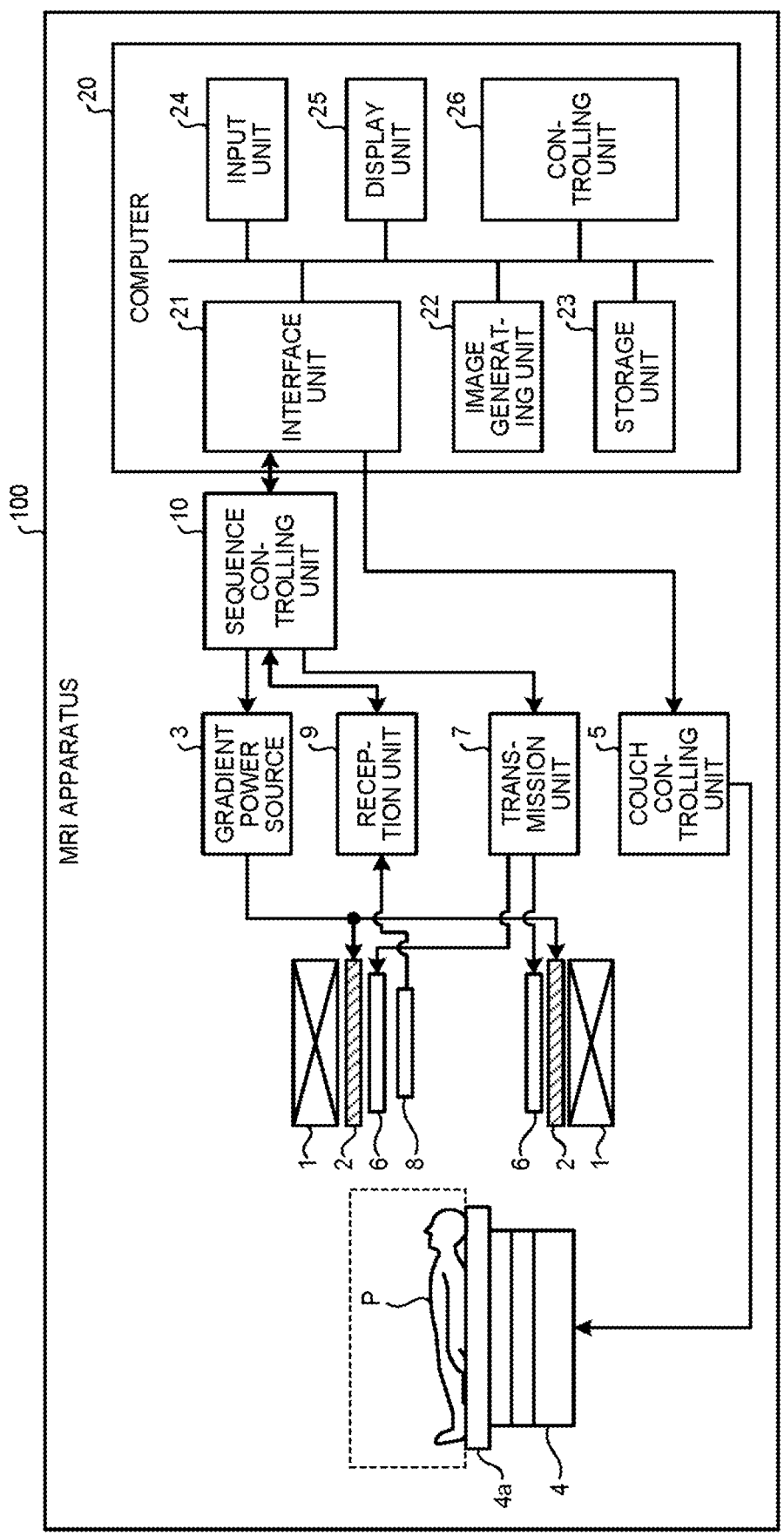
FIG. 1 is a block diagram of an MRI apparatus according to a first embodiment.

FIG. 1 is a block diagram of an MRI apparatus 100 according to a first embodiment. As illustrated in FIG. 1, the MRI apparatus 100 includes a magnetostatic field magnet 1, a gradient coil 2, a gradient power source 3, a couch 4, a couch controlling unit 5, a transmission coil 6, a transmission unit 7, a reception coil 8, a reception unit 9, a sequence controlling unit 10, and a computer 20. The MRI apparatus 100 does not include an examined subject (hereinafter, "patient") P (e.g., a human body) indicated in the dotted-line frame in FIG. 1. The configuration illustrated in FIG. 1 is merely an example. For instance, any of the functional units in the sequence controlling unit 10 and the computer 20 may be integrated together or configured separately, as appropriate.

The magnetostatic field magnet 1 is a magnet formed in the shape of a hollow circular cylinder (which may have an oval cross-section orthogonal to the axis thereof) and is configured to generate a magnetostatic field in the space on the inside thereof. The magnetostatic field magnet 1 may be configured by using, for example, a permanent magnet. Alternatively, the magnetostatic field magnet 1 may be configured by using a superconductive magnet. When the magnetostatic field magnet 1 is configured by using a superconductive magnet, the MRI apparatus 100 includes a magnetostatic field power source (not illustrated), which is configured to supply an electric current to the magnetostatic field magnet 1. In that situation, the magnetostatic field magnet 1 is configured to be excited by receiving the supply of electric current from the magnetostatic field power source. Alternatively, the magnetostatic field power source may be provided separately from the MRI apparatus 100.

The gradient coil 2 is a coil formed in the shape of a hollow circular cylinder (which may have an oval cross-section orthogonal to the axis thereof) and is disposed on the inside of the magnetostatic field magnet 1. The gradient coil 2 is formed by combining three coils corresponding to X-, Y-, and Z-axes that are orthogonal to one another. These three coils individually receive a supply of electric current from the gradient power source 3 and generate gradient magnetic fields of which the magnetic field intensities change along the X-, Y-, and Z-axes. The gradient magnetic fields along the X-, Y-, and Z-axes generated by the gradient coil 2 are, for example, a slice-purpose gradient magnetic field Gs, a phase-encoding-purpose gradient magnetic field Ge, and a reading-purpose gradient magnetic field Gr. The gradient power source 3 is configured to supply the electric current to the gradient coil 2.

The couch 4 includes a couchtop 4a on which the patient P is placed. Under control of the couch controlling unit 5, while the patient P is placed thereon, the couchtop 4a is inserted into the hollow (i.e., an image taking opening) of the gradient coil 2. Normally, the couch 4 is provided so that the longitudinal direction thereof extends parallel to the central axis of the magnetostatic field magnet 1. Under control of the computer 20, the couch controlling unit 5 drives the couch 4 so that the couchtop 4a moves in longitudinal directions and in up-and-down directions.

The transmission coil 6 is disposed on the inside of the gradient coil 2 and is configured to generate a radio-frequency magnetic field by receiving a supply of an RF pulse from the transmission unit 7. The transmission unit 7 is configured to supply the RF pulse corresponding to a Larmor frequency determined by the type of targeted atoms and the magnetic field intensities, to the transmission coil 6.

The reception coil 8 is disposed on the inside of the gradient coil 2 and is configured to receive Magnetic Resonance signals (hereinafter, "MR signals", as appropriate) emitted from the patient P due to an influence of the radio frequency magnetic field. When having received the MR signals, the reception coil 8 outputs the received MR signals to the reception unit 9.

The transmission coil 6 and the reception coil 8 described above are merely examples. The configurations thereof may be realized by selecting one of the following or combining together two or more of the following: a coil having only a transmitting function; a coil having only a receiving function; and a coil having transmitting and receiving functions.

The reception unit 9 is configured to detect the MR signals output from the reception coil 8 and to generate MR data on the basis of the detected MR signals. More specifically, the reception unit 9 generates the MR data by applying a digital conversion to the MR signals output from the reception coil 8. Further, the reception unit 9 is configured to transmit the generated MR data to the sequence controlling unit 10. The reception unit 9 may be provided on the gantry device side where the magnetostatic field magnet 1, the gradient coil 2, and the like are provided.

The sequence controlling unit 10 is configured to perform an image taking process on the patient P, by driving the gradient power source 3, the transmission unit 7, and the reception unit 9, on the basis of sequence information transmitted from the computer 20. In this situation, the sequence information is information that defines a procedure for performing the image taking process. The sequence information defines: the intensity of the electric current to be supplied from the gradient power source 3 to the gradient coil 2 and the timing with which the electric current is to be supplied; the intensity of the RF pulse to be supplied from the transmission unit 7 to the transmission coil 6 and the timing with which the RF pulse is to be applied; the timing with which the MR signals are to be detected by the reception unit 9, and the like. For example, the sequence controlling unit 10 may be configured with an integrated circuit such as an Application Specific Integrated Circuit (ASIC) or a Field Programmable Gate Array (FPGA), or an electronic circuit such as a Central Processing Unit (CPU) or a Micro Processing Unit (MPU).

When having received the MR data from the reception unit 9, as a result of the image taking process performed on the patient P by driving the gradient power source 3, the transmission unit 7, and the reception unit 9, the sequence controlling unit 10 transfers the received MR data to the computer 20.

The computer 20 is configured to exercise overall control of the MRI apparatus 100, to generate images, and the like. The computer 20 includes an interface unit 21, an image generating unit 22, a storage unit 23, an input unit 24, a display unit 25, and a controlling unit 26.

The interface unit 21 is configured to transmit the sequence information to the sequence controlling unit 10 and to receive the MR data from the sequence controlling unit 10. Further, when having received the MR data, the interface unit 21 stores the received MR data into the storage unit 23. The MR data stored in the storage unit 23 is arranged into a k-space by the controlling unit 26. As a result, the storage unit 3 stores k-space data therein.

The image generating unit 22 is configured to read the k-space data from the storage unit 23 and to generate an image by performing a reconstructing process such as a Fourier transform on the read k-space data.

The storage unit 23 is configured to store therein, the MR data received by the interface unit 21, the k-space data arranged in the k-space by the controlling unit 26, image data generated by the image generating unit 22, and the like. The storage unit 23 is configured by using, for example, a semiconductor memory element such as a Random Access Memory (RAM) or a flash memory, a hard disk, an optical disk, or the like.

The input unit 24 is configured to receive various types of instructions and inputs of information from an user. For example, the input unit 24 may be configured by using a pointing device such as a mouse or a trackball and/or an input device such as a keyboard. The display unit 25 is configured to display, under the control of the controlling unit 26, various types of Graphical User Interfaces (GUIs), the image generated by the image generating unit and the like. For example, the display unit 25 may be configured by using a display device such as a liquid crystal display device.

The controlling unit 26 is configured to exercise overall control of the MRI apparatus 100 and to control image taking processes, image generating processes, image displaying processes, and the like. For example, the controlling unit 26 receives an input of an image taking condition via a GUI, generates the sequence information according to the received image taking condition, and transmits the generated sequence information to the sequence controlling unit 10. For example, the controlling unit 26 may be an integrated circuit such as an ASIC or an FPGA, or an electronic circuit such as a CPU or an MPU. As described later, the controlling unit 26 includes functional units that make it possible for the user to easily change cross-sectional positions of reference cross-sectional images. The reference cross-sectional images are one case of cross-sectional images.

Next, an outline of a process performed by the MRI apparatus 100 according to the first embodiment will be explained. For example, in the first embodiment, one or more protocols are set for performing one medical examination (hereinafter, "examination"). The aggregate of protocols (a protocol group) set for the examination will be referred to as examination protocols. According to one protocol, for instance, an image taking process in accordance with one pulse sequence is performed. In another example, according to one protocol, for instance, an image taking process in accordance with one pulse sequence and an image processing process using the taken data are performed.

The MRI apparatus 100 is configured to perform various types of operations according to one or more protocols contained in an aggregate of examination protocols. First, prior to an acquisition of reference cross-sectional images using imaging scans, it is necessary to set cross-sectional positions of the reference cross-sectional images which vary for each patient, in accordance with the position, the angle, and the like of a target site (a target). Accordingly, for example, the MRI apparatus 100 acquires multi-slice images and performs a cross-sectional position detecting process by using the multi-slice images, according to a protocol (named "cross-section detecting protocol") that defines various types of image taking conditions used for acquiring the multi-slice images and various types of conditions and the like used for detecting the cross-sectional positions of the reference cross-sectional images. In the following explanations, the protocol named "cross-section detecting protocol" will simply be referred to as "cross-section detecting protocol". For example, the MRI apparatus 100 acquires the multi-slice images according to the cross-section detecting protocol and stores the acquired multi-slice images into the storage unit 23. Further, for example, according to the cross-section detecting protocol, the MRI apparatus 100 automatically detects the cross-sectional positions of a plurality of reference cross-sectional images from the multi-slice images. To explain with a more detailed example, the MRI apparatus 100 automatically detects each of the cross-sectional positions by automatically detecting a characteristic site related to the target site from the multi-slice images and calculating the cross-sectional position by using the position of the automatically-detected characteristic site. For example, the MRI apparatus 100 is configured to detect cross-sectional positions of fourteen types of reference cross-sectional images. In this situation, the cross-sectional positions of the fourteen types of reference cross-sectional images are represented by the cross-sectional position of each of the following images: a left ventricular vertical long-axis image, a left ventricular horizontal long-axis image, a left (right) ventricular short-axis image, a left (right) ventricular two-chamber long-axis image, a left (right) ventricular three-chamber long-axis image, a left (right) ventricular four-chamber long-axis image, a left (right) ventricular outflow tract image, an aortic valve image, and a pulmonary valve image. Further, for example, the MRI apparatus 100 generates a plurality of reference cross-sectional images on the basis of the automatically-detected cross-sectional positions, generates a localizer screen on which the generated plurality of reference cross-sectional images are arranged, and displays the localizer screen. In that situation, the MRI apparatus 100 displays, in the reference cross-sectional images, a mark indicating the position of a characteristic site related to the target site and a mark indicating the position and the direction of an intersecting line expressing the position and the direction in which the cross-sectional position of the reference cross-sectional image intersects the cross-sectional position of another reference cross-sectional image. In this situation, while checking the reference cross-sectional images displayed on the localizer screen, the user is able to change, by operating the input unit 24, the cross-sectional position of each of the reference cross-sectional images, by changing the position of the mark indicating the characteristic site so as to change the position of the characteristic site and by changing the mark indicating the position and the direction of the intersecting line so as to change the position and the direction of the intersecting line. In this manner, the user is able to check and change the reference cross-sectional images displayed on the localizer screen.

An imaging scan is, for example, an image taking process (which may be called "a main image taking process") performed to acquire one or more images primarily used for a diagnosis purpose. A preparatory scan is, for example, an image taking process (which may be called "a preparatory image taking process") that is typically performed prior to the imaging scan.

Further, one aggregate of examination protocols includes, for example, at least one protocol that defines an image taking condition and the like to be used when an imaging scan is performed. In other words, during one examination, at least one imaging scan is performed. In the following sections, an example will be explained in which the target site is the "heart"; however, the target site does not necessarily have to be the "heart". To perform an examination on cardiac functions of the left ventricular system of the heart, for example, an imaging scan to acquire a left ventricular short-axis image, an imaging scan to acquire a left ventricular two-chamber long-axis image, an imaging scan to acquire a left ventricular three-chamber long-axis image, and an imaging scan to acquire a left ventricular four-chamber long-axis image are performed. As another example, to perform an examination on the right ventricular system of the heart, for instance, an imaging scan to acquire a right ventricular short-axis image, an imaging scan to acquire a right ventricular two-chamber long-axis image, an imaging scan to acquire a right ventricular three-chamber long-axis image, and an imaging scan to acquire a right ventricular four-chamber long-axis image are performed. In other words, the types of the reference cross-sectional images acquired by performing imaging scans during an examination vary depending on the purpose of the examination. Thus, depending on the purpose of an examination, the types of examinations to be performed in order to achieve the purpose of the examination vary. It is therefore considered that the types of the reference cross-sectional images acquired by performing imaging scans during an examination vary depending on the type of the examination.

The multi-slice images are represented by data including a plurality of slice images acquired by using a two-dimensional (2D) sequence. The multi-slice images serve as an example of three-dimensional data. In place of the multi-slice images, it is also acceptable to use volume data acquired by using a three-dimensional (3D) sequence. In this situation, the 2D sequence is a pulse sequence for acquiring one or more two-dimensional cross-sectional images by performing an encoding process in a phase-encoding direction and a read-out direction, with respect to one or more positions along the slice direction. Further, the 3D sequence is a pulse sequence for acquiring three-dimensional volume data by performing an encoding process not only in the phase-encoding direction and the read-out direction, but also in the slice direction. Alternatively, the 2D sequence and the 3D sequence described above may each be a radial scan sequence for acquiring the read-out direction at various angles.

Further, from the multi-slice images, the MRI apparatus 100 generates a plurality of types of reference cross-sectional images corresponding to the automatically-detected plurality of cross-sectional positions. For example, the MRI apparatus 100 generates the fourteen types of reference cross-sectional images described above.

In most examinations, it is often the case that the number of types of reference cross-sectional images observed by the user (e.g., a medical doctor or a medical radiology technician) on the localizer screen (observation-target reference cross-sectional images) is only several types at, most. Accordingly, during an examination, if all the types of reference cross-sectional images that are generated are displayed on the display unit 25 for the purpose of performing the localizer process on the reference cross-sectional images, even some reference cross-sectional images that are not the observation targets and are less relevant to the examination are displayed. Thus, the observation-target reference cross-sectional images that are considered to be more relevant to the examination and the reference cross-sectional images that are not the observation targets are displayed in a mixed manner. For this reason, in some situations, the user may find it difficult to observe the observation-target, reference cross-sectional images. In those situations, the user may not be able to easily perform the localizer process on the reference cross-sectional images.

To cope with these situations, the MRI apparatus 100 according to the first embodiment is configured to aid a layout generating process so as to display certain types of reference cross-sectional images that are among the generated reference cross-sectional images and are suitable for the type of the examination currently performed. Further, by using the generated layout, the MRI apparatus 100 according to the first embodiment causes the display unit 25 to display the types of reference cross-sectional images that are among the generated reference cross-sectional images and are suitable for the type of the currently-performed examination. With this arrangement, the displayed reference cross-sectional images are limited to the observation-target reference cross-sectional images. As a result, the MRI apparatus 100 makes it possible for the user to easily observe the observation-target reference cross-sectional images in the currently-performed examination. Consequently, the MRI apparatus 100 makes it possible for the user to easily perform the localizer process on the reference cross-sectional images.

Further, when the localizer process is completed on the cross-sectional positions of the plurality of reference cross-sectional images displayed on the display unit 25, the MRI apparatus 100 performs imaging scans in the cross-sectional positions on which the localizer process has been completed.

Figure 2:
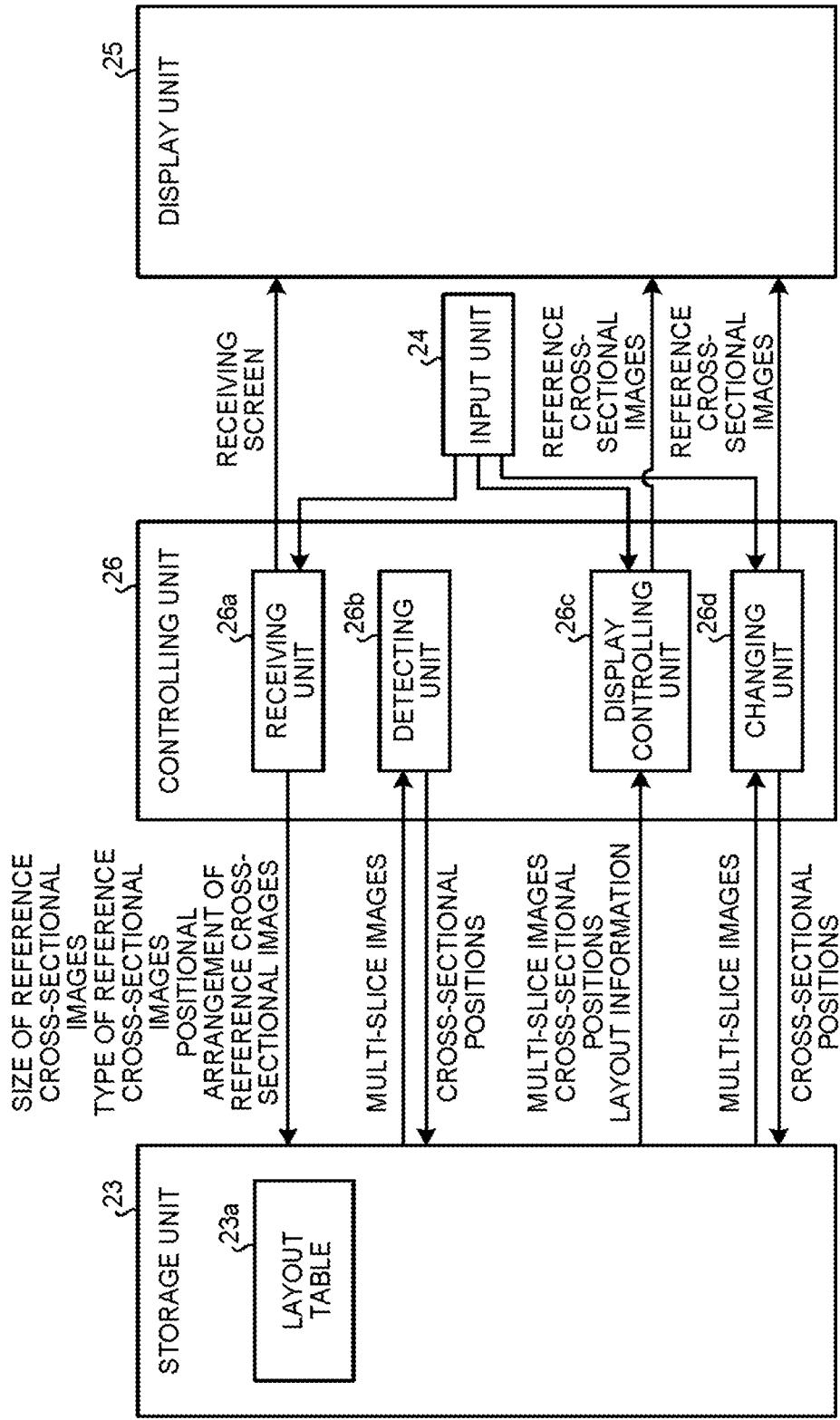
FIG. 2 is a block diagram of a controlling unit according to the first embodiment.

Next, the controlling unit 26 according to the first embodiment will be explained. FIG. 2 is a block diagram of the controlling unit 26 according to the first embodiment. As illustrated by the example in FIG. 2, the controlling unit 26 includes a receiving unit 26a, a detecting unit 26b, a display controlling unit 26c, and a changing unit 26d. Further, the storage unit 23 stores therein a layout table 23a.

The receiving unit 26a is configured to receive a type, a size, and a positional arrangement of reference cross-sectional images and stores the received type, size, and positional arrangement of the reference cross-sectional images into the storage unit 23. For example, the receiving unit 26a causes the display unit 25 to display a screen that receives the size of the reference cross-sectional images, a set of types of reference cross-sectional images, and the positional arrangement of the reference cross-sectional images. In this situation, the size of the reference cross-sectional images may be, for example, the size of a display area in which the reference cross-sectional images are displayed. Further, via the screen displayed on the display unit 25, the receiving unit 26a receives layout information indicating the size of the reference cross-sectional images, the set of types of reference cross-sectional images, and the positional arrangement of the reference cross-sectional images. In other words, the layout information is information that defines a layout (the size of the reference cross-sectional images, the set of types of reference cross-sectional images, and the positional arrangement of the reference cross-sectional images). Further, the receiving unit 26a registers the received layout information into the layout table 23a. In the layout table 23a, a plurality of pieces of layout information are registered by the receiving unit 26a. Accordingly, the layout table 23a has registered therein the plurality of pieces of layout information each of which defines a layout of reference cross-sectional images displayed on the localizer screen. The layout table 23a will be explained later.

The detecting unit 26b is configured to detect a plurality of cross-sectional positions from already-acquired data such as for example, the multi-slice images. For example, the detecting unit 26b obtains the multi-slice images acquired in a preparatory scan and stored in the storage unit 23, from the storage unit 23, and automatically detect the cross-sectional positions of the plurality of types of reference cross-sectional images, from the obtained multi-slice images. For example, the detecting unit 26b detects the cross-sectional positions of the fourteen types of cross-sectional images described above. After that, the detecting unit 26b stores the automatically-detected plurality of cross-sectional positions into the storage unit 3.

The display controlling unit 26c is configured to display, on the localizer screen, all or a part of the plurality of reference cross-sectional images generated on the basis of the plurality of cross-sectional positions, according to at least one of the plurality of pieces of layout information.

A mode of the display controlling unit 26c will be explained. The display controlling unit 26c is configured to generate the plurality of types of reference cross-sectional images corresponding to the plurality of cross-sectional positions. For example, the display controlling unit 26c first obtains the multi-slice images and the plurality of cross-sectional positions from the storage unit 23 and generates, from the obtained multi-slice images, the plurality of types of reference cross-sectional images respectively corresponding to the obtained plurality of cross-sectional positions, by performing a Multi-Planar Reconstruction (MPR) process.

After that, the display controlling unit 26c causes the display unit 25 to display the types of reference cross-sectional images that are among the plurality of types of reference cross-sectional images and are suitable for the type of the examination. In this situation, the display controlling unit 26c displays, in the reference cross-sectional images, a mark indicating a characteristic site related to the heart and a mark indicating the position and the direction of an intersecting line at which the cross-sectional position of the reference cross-sectional image intersects the cross-sectional position of another reference cross-sectional image. In this situation, as explained above, the user is able to change the cross-sectional position of any of the reference cross-sectional images, by changing the position of the mark indicating the characteristic site or changing the position and the direction of the intersecting line by operating the input unit 24.

When the user has changed the position of the characteristic site and/or the position and the direction of the intersecting line with respect to any of the reference cross-sectional images, the changing unit 26d is configured to calculate the cross-sectional position of a relevant reference cross-sectional image by using the position of the characteristic site after the change (hereinafter, "post-change position") and/or the post-change position and direction of the intersecting line. Further, the changing unit 26d stores the calculated cross-sectional position into the storage unit 23. After that, the changing unit 26d generates a reference cross-sectional image corresponding to the calculated cross-sectional position and updates the display by replacing the reference cross-sectional image before the change is made to the cross-sectional position, with the newly-generated reference cross-sectional image after the change is made to the cross-sectional position. For example, the changing unit 26d first obtains the multi-slice images from the storage unit 23. After that, the changing unit 26d generates, from the multi-slice images, the reference cross-sectional image corresponding to the calculated cross-sectional position by performing the MPR process and updates the display by replacing the reference cross-sectional image before the changes is made to the cross-sectional position, with the newly-generated reference cross-sectional image after the changes is made to the cross-sectional position.

Figure 3:
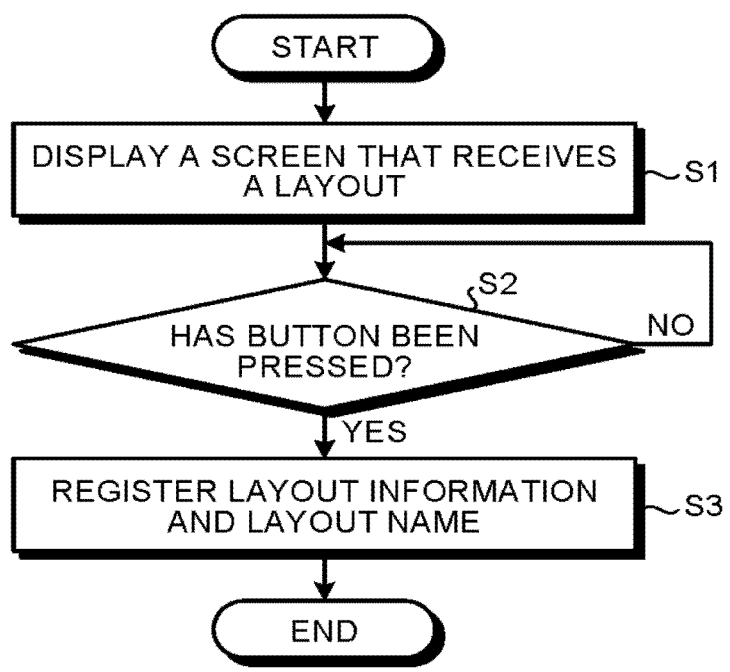
FIG. 3 is chart of an exemplary flow in a process performed by the MRI apparatus according to the first embodiment.

In the first embodiment, the layout information is registered regardless of the timing with which the examination is performed. For example, the layout information is registered in advance, prior to the examination. Next, a flow in the process of registering the layout information performed by the MRI apparatus 100 according to the first embodiment will be explained. FIG. 3 is a chart of an exemplary flow in the process performed by the MRI apparatus 100 according to the first embodiment.

Figure 4:
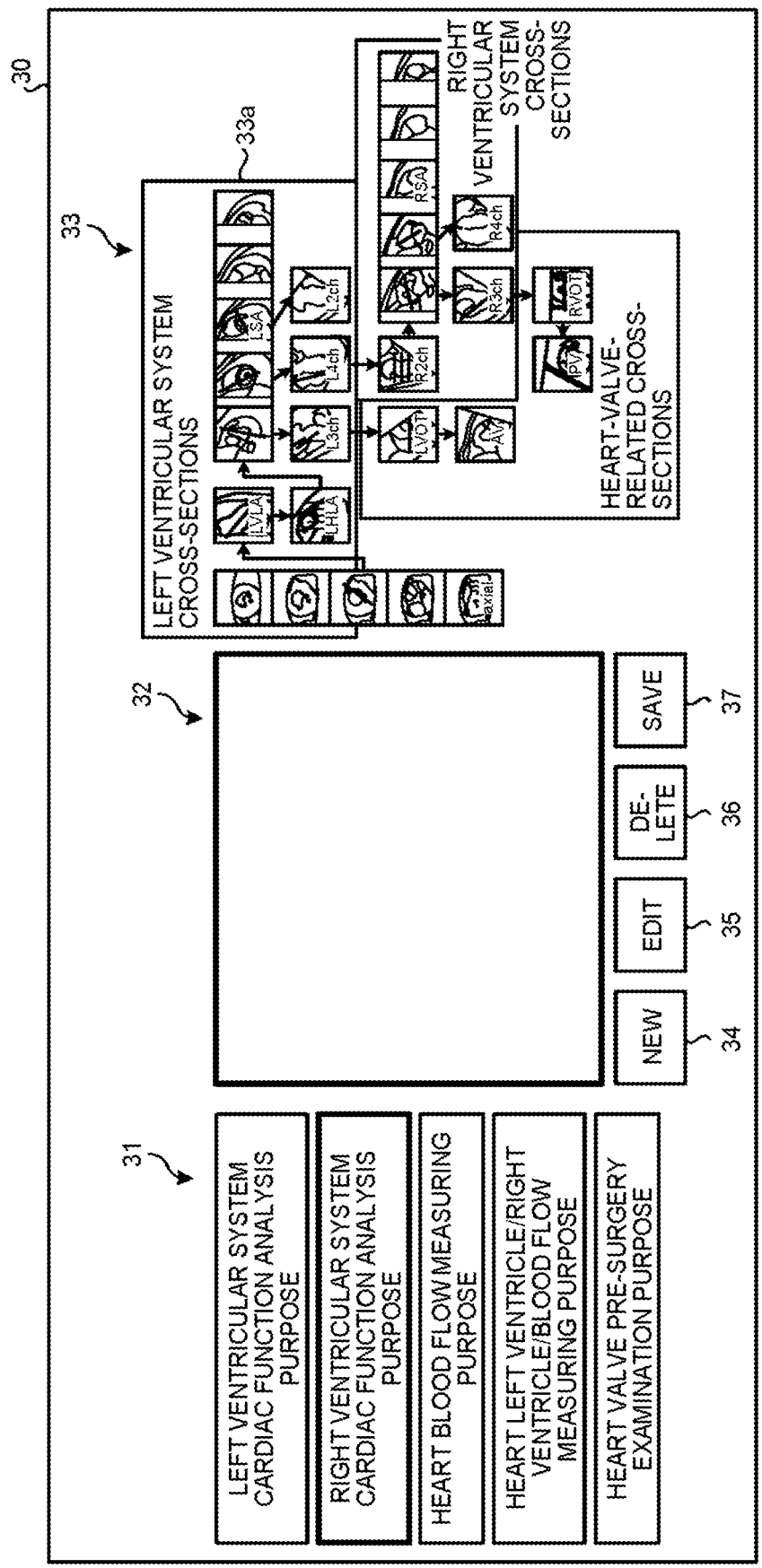
FIG. 4 is a drawing of an example of a screen that receives a layout according to the first embodiment.

First, the receiving unit 26a causes the display unit 25 to display a screen (a receiving screen) that receives a registration of the layout information (step S1). FIG. 4 is a drawing of an example of a screen 30 that receives the layout information according to the first embodiment. As illustrated by the example in FIG. 4, the receiving unit 26a causes the display unit 25 to display the screen 30. The screen 30 includes areas 31 to 33 and buttons 34 to 37. In the area 31, a list of layout names is displayed. The area 32 is an area in which a layout is generated. The area 33 is an area in which a correlation diagram 33a of reference cross-sectional images is displayed. The button 34 says "new". The button 35 says "edit". The button 36 says "delete". The button 37 says "save".

Next, the correlation diagram 33a of the reference cross-sectional images will be explained. The correlation diagram 33a indicates an example of a general procedure to be performed when reference cross-sectional images are set manually.

The correlation diagram 33a in the example of FIG. 4 includes five body axis transversal cross-sectional images (axial) which are multi-slice images, one left ventricular vertical long-axis image (LVLA), one left ventricular horizontal long-axis image (LHLA), five left ventricular short-axis images (LSA), one left ventricular two-chamber long-axis image (L2ch), one left ventricular three-chamber long-axis image (L3ch), one left ventricular four-chamber long-axis image (L4ch), five right ventricular short-axis images (RSA), one right ventricular two-chamber long-axis image (R2ch), one right ventricular three-chamber long-axis image (R3ch), one right ventricular four-chamber long-axis image (R4ch), one left ventricular outflow tract image (LVOT), one right ventricular outflow tract image (RVOT), one aortic valve image (AV), and one pulmonary valve image (PV).

The correlation diagram 33a indicates that the cross-sectional position of the left ventricular vertical long-axis image is set by using one of the five body axis transversal cross-sectional images. Further, the correlation diagram 33a indicates that the cross-sectional position of the left ventricular horizontal long-axis image is set by using the left ventricular vertical long-axis image. Further, the correlation diagram 33a indicates that the cross-sectional positions of the five left ventricular short-axis images are set by using the left ventricular horizontal long-axis image. In addition, the correlation diagram 33a indicates that the cross-sectional position of the left ventricular three-chamber long-axis image is set by using one of the five left ventricular short-axis images. Further, the correlation diagram 33a indicates that the cross-sectional position of the left ventricular four-chamber long-axis image is set by using one of the five left ventricular short-axis images. Furthermore, the correlation diagram 33a indicates that the cross-sectional position of the left ventricular two-chamber long-axis image is set by using another one of the five left ventricular short-axis images.

Further, the correlation diagram 33a indicates that the cross-sectional position of the right ventricular two-chamber long-axis image is set by using the left ventricular four-chamber long-axis image. Further, the correlation diagram 33a indicates that the cross-sectional positions of the five right ventricular short-axis images are set by using the right ventricular two-chamber long-axis image. Further, the correlation diagram 33a indicates that the cross-sectional position of the right ventricular three-chamber long-axis image is set by using one of the five right ventricular short-axis images. Further, the correlation diagram 33a indicates that the cross-sectional position of the right ventricular four-chamber long-axis image is set by using another one of the five right ventricular short-axis images.

In addition, the correlation diagram 33a indicates that the cross-sectional position of the left ventricular outflow tract image is set by using the left ventricular three-chamber long-axis image. Further, the correlation diagram 33a indicates that the cross-sectional position of the aorta valve image is set by using the left ventricular outflow tract image. Furthermore, the correlation diagram 33a indicates that the cross-sectional position of the right ventricular outflow tract image is set by using the right ventricular three-chamber long-axis image. Further, the correlation diagram 33a indicates that the cross-sectional position of the pulmonary valve image is set by using the right ventricular outflow tract image.

Further, in the correlation diagram 33a, to enable the user to easily generate a layout in which the displayed reference cross-sectional images are limited to observation-target reference cross-sectional images, the reference cross-sectional images are organized into groups corresponding to types of examinations. In the example illustrated in FIG. 4, the correlation diagram 33a indicates that the reference cross-sectional images of the left ventricle of the heart belong to the group for examination of "left ventricular system cross-sections" of which the observation targets are reference cross-sectional images of the left ventricle of the heart (the examination on the left ventricular system of the heart). Further, the correlation diagram 33a indicates that the reference cross-sectional images of the right ventricle of the heart belong to the group for the examination of "right ventricular system cross-sections" of which the observation targets are reference cross-sectional images of the right ventricle of the heart (the examination on the right ventricular system of the heart). Further, the correlation diagram 33a indicates that reference cross-sectional images including a valve and the like belong to the group for the examination of "heart-valve-related cross-sections" which is performed to measure the blood flow rate near a valve and to check the manner in which the valve itself moves and of which the observation targets are reference cross-sectional images including the valve and the like.

In the example illustrated in FIG. 4, the user is able to register new layout information, to edit already-registered layout information, and to delete already-registered layout information, by operating the input unit 24.

Next, an example in which the user registers new layout information will be explained. For example, to register the new layout information, the user presses the button 34 by operating the input unit 24. When the button 34 is pressed, the receiving unit 26a displays a text box in which a layout name can be input in the area 31. Accordingly, the user inputs a layout name into the text box, by operating the input unit 24. For example, the user inputs "right ventricular system cardiac function analysis purpose" in the text box.

After that, by referring to the relationship indicated by the correlation diagram 33a of the reference cross-sectional images, the user arranges one of the reference cross-sectional images from among the correlation diagram 33a of the reference cross-sectional images into the area 32 by performing a drag-and-drop operation while using the mouse in the input unit 24. As a result, the receiving unit 26a receives the type and the positional arrangement, which are among the type, size, and positional arrangement of reference cross-sectional images defined by the layout information. Alternatively, the user is also able to select a plurality of reference cross-sectional images from the correlation diagram 33a and to arrange the plurality of reference cross-sectional images into the area 32 all at once by performing a drag-and-drop operation while using the mouse in the input unit 24. Further, the user is also able to select one of the groups written in the correlation diagram 33a (e.g., the group for the examination of "left ventricular system cross-sections") so as to arrange all of the reference cross-sectional images belonging to the selected group into the area 32.

Figure 5:
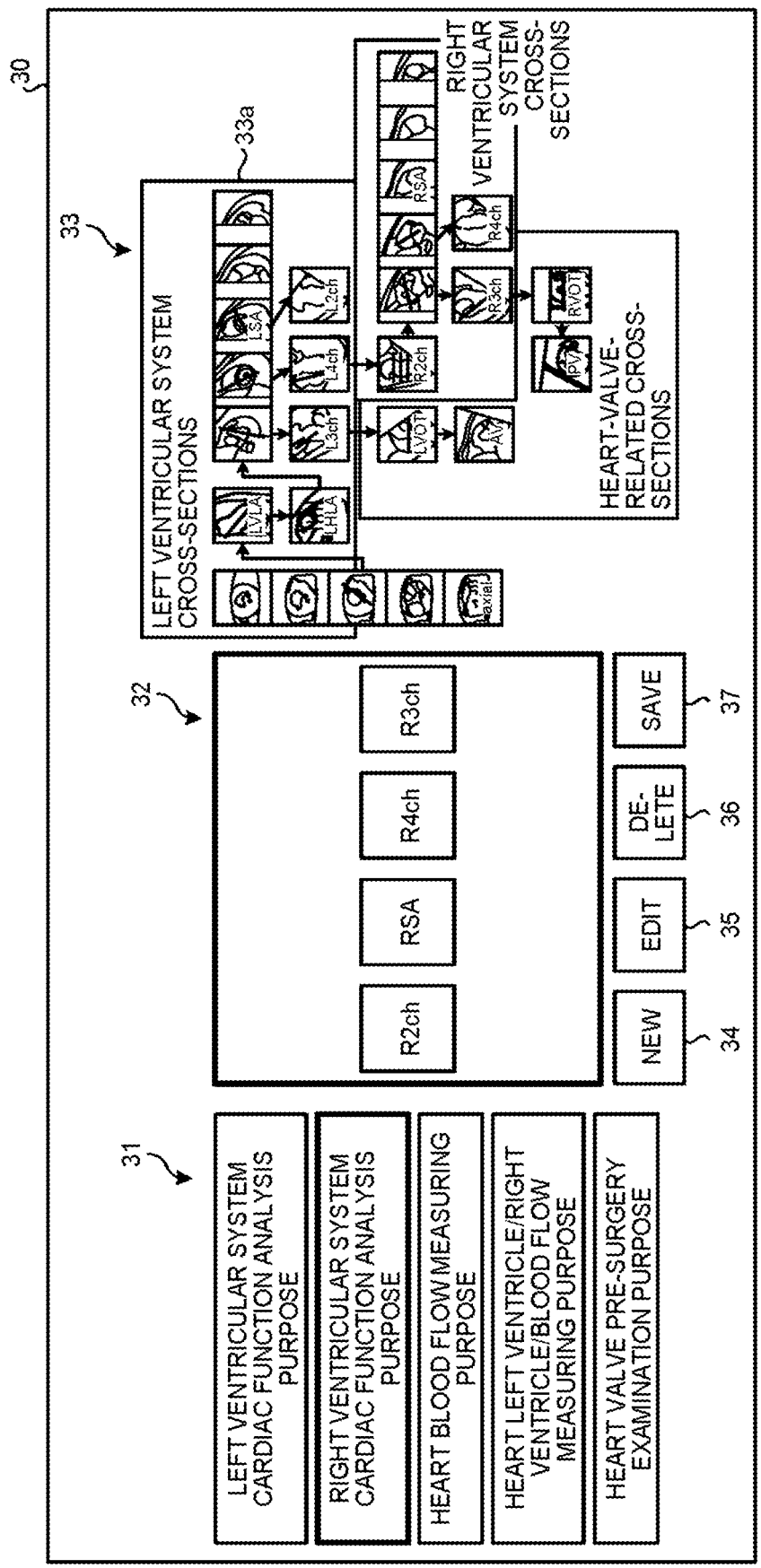
FIG. 5 is another drawing of the example of the screen that receives the layout according to the first embodiment.

In this situation, for example, let us discuss an example in which the user generates a layout so that, during an examination on the right ventricular system of the heart, the right ventricular two-chamber long-axis image (R2ch), the right ventricular short-axis image (RSA), the right ventricular four-chamber long-axis image (R4ch), and the right ventricular three-chamber long-axis image (R3ch) are displayed on the localizer screen from the left to the right. In that situation, the user arranges the reference cross-sectional images as illustrated by the example in FIG. 5. In other words, as illustrated in FIG. 5, the user arranges the right ventricular two-chamber long-axis image, the right ventricular short-axis image, the right ventricular four-chamber long-axis image, and the right ventricular three-chamber long-axis image from the left to the right in the area 32, by performing a drag-and-drop operation on the right ventricular two-chamber long-axis image, the right ventricular short-axis image, the right ventricular four-chamber long-axis image, and the right ventricular three-chamber long-axis image from the correlation diagram 33a, while checking the reference cross-sectional images organized in the group "right ventricular system cross-sections" and the setting procedure for the reference cross-sectional images indicated in the correlation diagram 33a.

When the right ventricular two-chamber long-axis image, the right ventricular short-axis image, the right ventricular four-chamber long-axis image, and the right ventricular three-chamber long-axis image have been arranged in the a 32, the receiving unit 26a receives the right ventricular two-chamber long-axis image, the right ventricular short-axis image, the right ventricular four-chamber long-axis image, and the right ventricular three-chamber long-axis image as the types of reference cross-sectional images. In this situation, when arranging these reference cross-sectional images in the area 32, the user arranges the reference cross-sectional images in such positions in the area 32 that correspond to desired positions on the localizer screen so that the reference cross-sectional images are arranged in the desired positions on the localizer screen from the left to the right. Accordingly, the receiving unit 26a receives the positions of the right ventricular two-chamber long-axis image, the right ventricular short-axis image, the right ventricular four-chamber long-axis image, and the right ventricular three-chamber long-axis image in the area 32, as the positional arrangement of the reference c sectional images. As explained above, because the MRI apparatus 100 presents the user with the observation-target reference cross-sectional images (i.e., the reference cross-sectional images organized into the group "right ventricular system cross-sections") for the examination on the right ventricular system of the heart, the MRI apparatus 100 makes it possible for the user to easily generate the layout in which the observation-target reference cross-sectional images for the examination on the right ventricular system of the heart are displayed. Further, because the MRI apparatus 100 presents the user with the procedure for manually setting the observation-target reference cross-sectional images for the examination on the right ventricular system of the heart, the MRI apparatus 100 makes it possible for the user to easily generate the layout in which the observation-target reference cross-sectional images for the examination on the right ventricular system of the heart are displayed together with other reference cross-sectional images that are set immediately prior to the reference cross-sectional images, when reference cross-sectional images are set manually. Further, for example, it is effective in checking the positions of the observation-target reference cross-sectional images to display the reference cross-sectional images that are close, in the course of the manual setting procedure, to the observation-target reference cross-sectional images on the localizer screen together, even if the images are not the observation targets. Consequently, the system of generating the layout from the correlation diagram 33a is also effective as an aid for generating the practical layout as described above.

Further, when changing the size of the reference cross-sectional images, the user changes the size of the reference cross-sectional images arranged in the area 32, by operating the input unit 24. The receiving unit 26a thus receives the size of the reference cross-sectional images defined by the layout information.

After that, the receiving unit 26a judges whether the button 37 has been pressed by the user (step S2). When it is determined that the button 37 has not been pressed (step S2: No), the receiving unit 26a performs the judging process at step S2 again.

On the contrary, when it is determined that the button 37 has been pressed (step S2: Yes), the receiving unit 26a registers layout information. For example, in the example illustrated in FIG. 5, when the button 37 is pressed, the receiving unit 26a registers the layout information indicating the four types, namely the right ventricular two-chamber long-axis image, the right ventricular short-axis image, the right ventricular four-chamber long-axis image, and the right ventricular three-chamber long-axis image, as well as the size and the positional arrangement of the four types of reference cross-sectional images into the layout table 23a so as to be kept in correspondence with the layout name "right ventricular system cardiac function analysis purpose" that was input (step S3).

Next, a data structure of the layout table 23a will be explained. The layout table 23a has the items "layout name" and "layout information". In each record of the layout table 23a, various types of information corresponding to one layout are registered. Under the item "layout name", layout names are registered by the receiving unit 26a. Under the item "layout information", layout information is registered by the receiving unit 26a.

Next, an example corresponding to the situation where the button 37 is pressed in the example in FIG. 5 described above will be explained. In that situation, the receiving unit 26a newly adds, to the layout table 23a, a record registering therein layout information indicating "right ventricular system cardiac function analysis purpose" under the item "layout name" and indicating the four types, namely the right ventricular two-chamber long-axis image, the right ventricular short-axis image, the right ventricular four-chamber long-axis image, and the right ventricular three-chamber long-axis image under the item "layout information", as well as the size and the positional arrangement of the four types of reference cross-sectional images. The new layout information is registered in this manner. Furthermore, plurality of pieces of registered layout information is defined according to a type of an image taking process included in an examination protocol.

Next, an example will be explained in which the user edits already-registered layout information. In that situation, the user selects the layout name of the layout information to be edited, from the list of layout names displayed in the area 31, by operating the input unit 24. When the layout name is selected, the receiving unit 26a refers to the layout table 23a and identifies the record in which the selected layout name is registered under the item "layout name". Further, the receiving unit 26a obtains the layout information registered in the identified record under the item "layout information".

After that, the receiving unit 26a displays, in the area 32, the layout (the size, the set of types, and the positional arrangement of the reference cross-sectional images) indicated by the obtained layout information. When the button 35 is pressed by the user while the layout is being displayed, the receiving unit 26a changes the state of the displayed layout so as to be editable by the user. Further, by operating the input unit 24, the user edits the layout by changing the size, changing the set of types, and/or changing the positional arrangement of the reference cross-sectional images displayed in the area 32. When having completed the editing process, the user presses the button 37. When the button 37 is pressed, the receiving unit 26a updates the layout information indicated by the pre-edit layout registered in the layout table 23a, with the layout information indicated by the post-edit layout. The already-registered layout information is edited in this manner.

Next, an example will be explained in which the user deletes already-registered layout information. In that situation, by operating the input unit 24, the user selects the layout name of the layout information to be deleted from the list of layout names displayed in the area 31. When the layout name is selected, the receiving unit 26a refers to the layout table 23a and identifies the record in which the selected layout name is registered under the item "layout name". Further, the receiving unit 26a obtains the layout information registered in the identified record under the item "layout information".

After that, the receiving unit 26a displays, in the area 12, the layout indicated by the obtained layout information. When the button 36 is pressed by the user while the layout is being displayed, the receiving unit 26a deletes the identified record from the layout table 23a. The already-registered layout information is deleted in this manner.

The examples of the various processes of registering the new layout information, editing the already-registered layout information, and deleting the already-registered layout information have thus been explained.

In the first embodiment, in the cross-section detecting protocol, the user sets, in advance, according to which piece of layout information the reference cross-sectional images are to be detected and displayed, while the user takes into consideration the types of examinations included in the examination protocols to which the cross-section detecting protocol belongs. Further, the cross-section detecting protocol with which the layout information is set is saved in the storage unit 23, as a part of the examination protocols. For example, the cross-section detecting protocol is set with such layout information that indicates a layout in which the observation-target, reference cross-sectional images that are considered to be highly relevant to the examinations included in the examination protocols to which the cross-section detecting protocol belongs are displayed and in which the reference cross-sectional images that are not the observation targets are not displayed.

For example, with a cross-section detecting protocol belonging to "right ventricular system examination", which is a general term for a group of protocols for the purpose of examining the right ventricle of the heart, layout information of which the layout name is "right ventricular cardiac function analysis purpose" is set.

Figure 6:
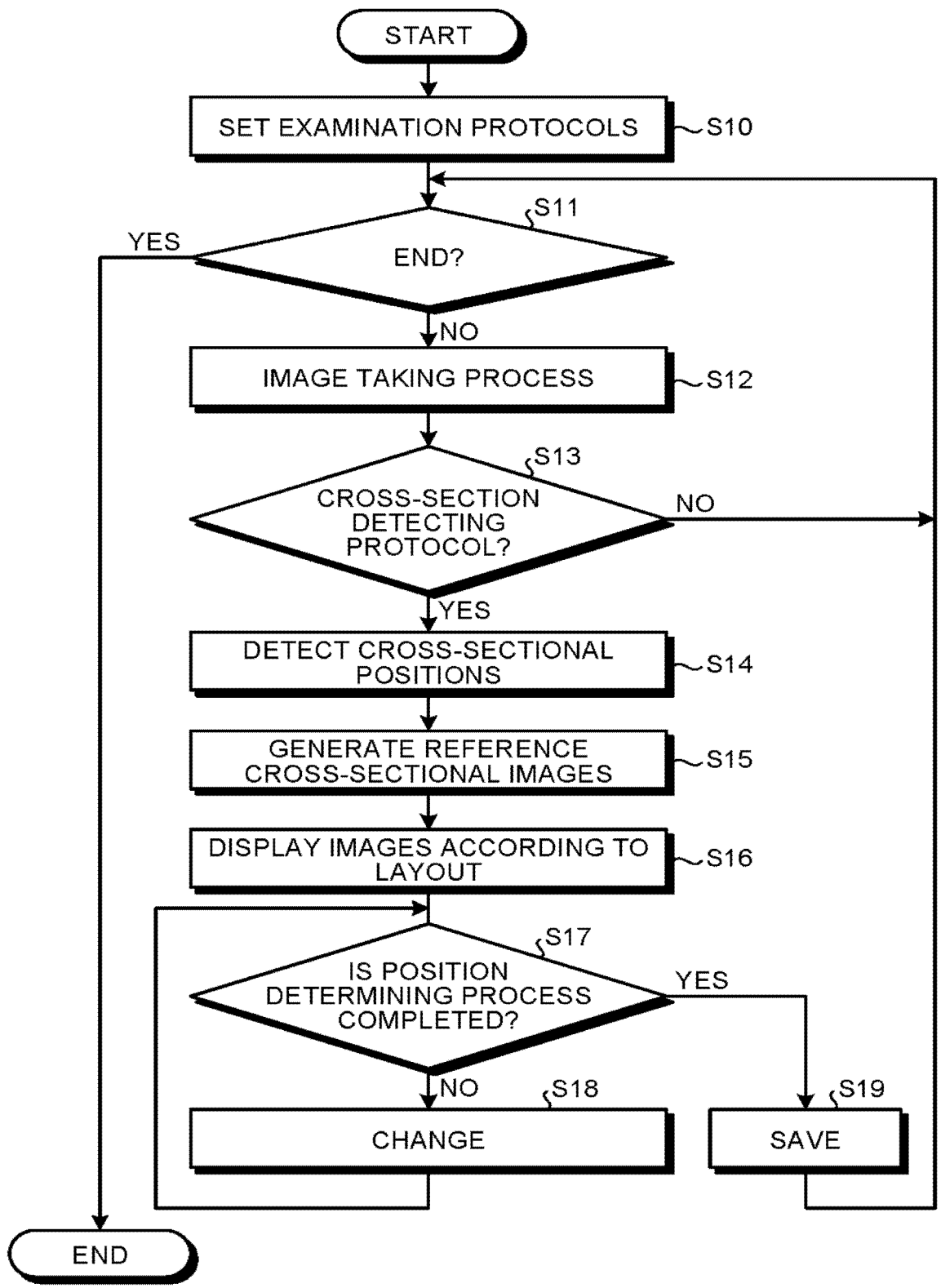
FIG. 6 is a flowchart of a processing procedure according to the first embodiment.

Next, a flow in a process performed by the MRI apparatus 100 when an examination is performed will be explained. FIG. 6 is a flowchart of a processing procedure when an examination is performed according to the first embodiment. In this situation, it is assumed that the cross-section detecting protocol is a protocol defining that the cross-sectional positions of the fourteen types of reference cross-sectional images described above are detected. However, the cross-section detecting protocol may be a protocol defining that the cross-sectional positions of the reference cross-sectional images corresponding to the types indicated by the layout information set with the protocol should be detected and that reference cross-sectional images corresponding to the types indicates by the layout information should be generated. In that situation, it is possible to decrease the number of cross-sectional positions to be detected and the number of reference cross-sectional images to be generated, and it is therefore possible to reduce the processing amounts.

As illustrated by the example in FIG. 6, the receiving unit 26a receives a setting of examination protocols for the examination to be performed (step S10).

Figure 7:
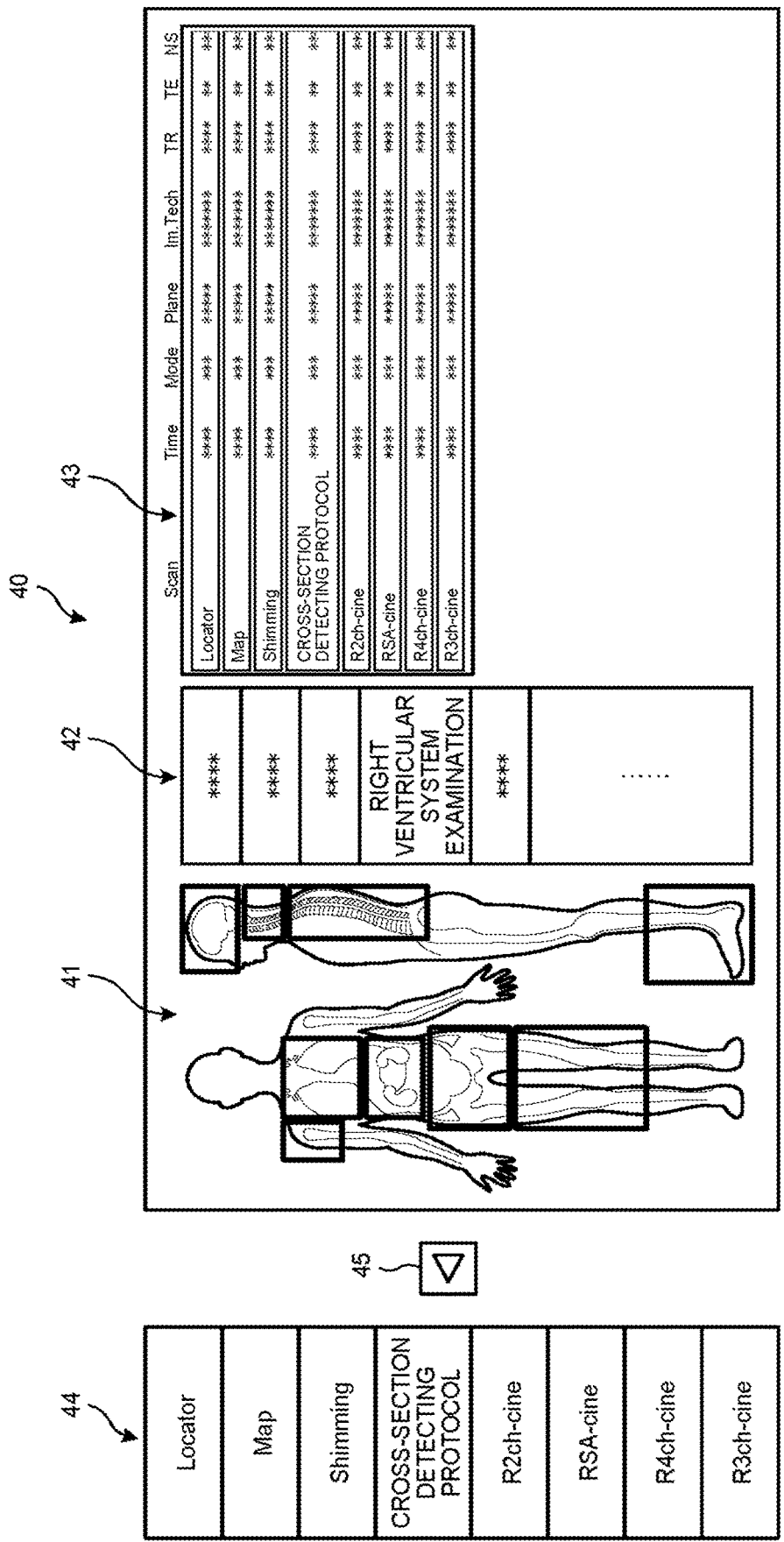
FIG. 7 is a drawing of an example a screen displayed at step S10 according to the first embodiment.

Next, an example will be explained in which a setting of examination protocols is received with respect to an examination to be performed. First, the receiving unit 26a causes the display unit 25 to display a screen that receives the setting of examination protocols. FIG. 7 is a drawing of an example of a screen 40 displayed at step S10 according to the first embodiment. For example, at step S10, the receiving unit 26a causes the display unit 25 to display the screen 40. The screen 40 includes areas 41 to 44 and a button 45.

In the area 41, a human body model diagram is displayed to receive a selection of each of the image taking sites. In the area 42, a list of general terms is displayed, the general terms each representing a group of protocols for image taking purposes (the protocol group) that is set in advance with respect to each of the image taking sites selected in the area 41. In the area 43, a list of the names of the protocols included in the protocol group that is set in advance with respect to each of the general terms selected in the area 42 is displayed. In the area 43, various types of image taking conditions are also displayed in addition to the names of the protocols. In the area 44, the names of the protocols included in the examination protocols set for the examination to be performed are displayed. For example, by sequentially selecting items in the areas 41, 42, and 43 on the display screen 40 in the stated order according to the hierarchical structure, the user sets the desired set of protocols to be implemented for the specific examination.

For example, when the user selects the rectangle corresponding to the "heart" in the area 41 by operating the input unit 24, the receiving unit 26a displays, in the area 42, a list of general terms of the protocol groups for an image taking process performed on the "heart". Subsequently, when the user selects the general term "right ventricular system examination" of the protocol group for the purpose of examining the right ventricle of the heart from the area 42 by operating the input unit 24, the receiving unit 26a displays, in the area 43, a list, of protocol names included in the protocol group indicated by the "right ventricular system examination" and the image taking conditions thereof. In the example illustrated in FIG. 7, the receiving unit 26a displays, in the area 43, "Locator", "Map", "Shimming", "cross-section detecting protocol", "R2ch-cine", "RSA-cine" "R4ch-cine", and "R3ch-cine".

In this situation, "Locator" is the name of a protocol defining various types f image taking conditions to acquire a locator image. Further, "Map" is the name of a protocol defining various types of image taking conditions to acquire a sensitivity map indicating the sensitivity of each of a plurality of coils structuring the reception coil 8. Further, "Shimming" is the name of a protocol defining various types of image taking conditions to perform a shimming process to correct the distribution of the magnetostatic field and to set a central frequency). Further, "R2ch-cine" is the name of a protocol defining various types of image taking conditions and the like to acquire the right ventricular two-chamber long-axis image through a cine imaging process. Further, "RSA-cine" is the name of a protocol defining various types of image taking conditions and the like to acquire the right ventricular short-axis image through a cine imaging process. Further, "R4ch-cine" is the name of a protocol defining various types of image taking conditions and the like to acquire the right ventricular four-chamber long-axis image through a cine imaging process. Further, "R3ch-cine" is the name of a protocol defining various types of image taking conditions and the like to acquire the right ventricular three-chamber long-axis image through a cine imaging process. In the following explanations, the protocol named "Locator", the protocol named "Map", the protocol named "Shimming", the protocol named "R2ch-cine", the protocol named "RSA-cine", the protocol named "R4ch-cine", and the protocol named "R3ch-cine" will simply be referred to as "Locator", "Map", "Shimming", "R2ch-cine", "RSA-cine", "R4ch-cine", and "R3ch-cine".

After that, by operating the input unit 24, the user selects one or more protocol names to be set for the examination to be performed, from among the list of protocol names displayed in the area 43 and presses the button 45. In the present example, a situation will be explained in which the user selects all of the protocol names displayed in the area 43 and presses the button 45. When the button 45 is pressed, the receiving unit 26a displays all of the selected protocol names in the area 44, and also, sets all of the protocols identified by the selected names as the examination protocols. In this manner, at step S10, the setting of the examination protocols is received for the examination to be performed. Alternatively, another arrangement is acceptable in which, when the user presses the button 45 while one of the general terms of the protocol groups displayed in the area 42 is being selected, the receiving unit 26a displays all of the protocol names displayed in the area 43 in the area 44, so that all of the protocols identified by the selected names are set as the examination protocols.

In this situation, the protocols included in the examination protocols that were set are sequentially extracted, so as to perform image taking processes to acquire various types of data and perform image processing processes according to the extracted protocols. For example, according to the examination protocols set in the example in FIG. 7, at first "Locator" is extracted, and when a locator image is acquired according to the extracted "Locator", "Map" is subsequently extracted. According to the extracted "Map", differences among the sensitivity levels of the plurality of coils included in the reception coil 8 are acquired. After that, "Shimming", "cross-section detecting protocol", "R2ch-cine", "RSA-cine", "R4ch-cine", and "R3ch-cine" are sequentially extracted in a similar manner, so as to perform various types of image taking processes and image processing processes according to the extracted protocols. In the first embodiment, some of the protocols with which neither an image taking process to acquire various types of data nor an image processing process has been performed will be referred to as "not-yet-acquired protocols".

Returning to the description of FIG. 6, the sequence controlling unit 10 judges whether there is any not-yet-acquired protocols in the protocols included in the examination protocols that were set (step S11). In this manner, it is determined whether the examination should be ended or not. When it is determined that there are one or more not-yet-acquired protocols, i.e., that the examination should not be ended (step S11: No), the sequence controlling unit 10 extracts the protocol that is the earliest in the sequential order from among the not-yet-acquired protocols and performs an image taking process according to the extracted protocol (step S12).

Next, an example in which the extracted protocol is the cross-section detecting protocol will be explained. In that situation, at step S12, the sequence controlling unit 10 and the image generating unit 22 perform various types of processes described below so as to acquire multi-slice images. In the first embodiment, the multi-slice images are, for example, a plurality of body axis transversal cross-sectional images. Further, the multi-slice images include images of the heart. While implementing an Electro Cardiogram (ECG) synchronization, the sequence controlling unit 10 drives the gradient power source 3, the transmission unit 7, and the reception unit 9 so as to acquire MR data of the multi-slice images while the patient is holding his/her breath and while the acquisition timing is limited to diastolic periods, for example. After that, the sequence controlling unit 10 transmits the acquired MR data to the image generating unit 22 via the interface unit 21. When having received the MR data, the image generating unit 22 generates the multi-slice images by using the received MR data and stores the generated multi-slice images into the storage unit 23. In this situation, the multi-slice images may be a plurality of sagittal cross-sectional images or coronal cross-sectional images. Further, the sequence controlling unit 10 uses, for example, a 2D Fast Field Echo (FEE), a 2D Steady-State Free Precession (SSFP), or the like, to acquire the MR data of the multi-slice images.

Next, an example will be explained in which the extracted protocol is a protocol defining image taking conditions and the like to perform an imaging scan. In that situation, at step S12, the sequence controlling unit 10 performs the imaging scan by using the cross-sectional position resulting from the localizer process and driving the gradient power source 3, the transmission unit 7, and the reception unit 9 according to the extracted protocol. The MR data obtained as a result of the imaging scan performed by the sequence controlling unit 10 is transmitted to the image generating unit 22 via the interface unit 21. When having received the MR data, the image generating unit 22 generates a reference cross-sectional image by using the received MR data and stores the generated reference cross-sectional image into the storage unit 23.

After that, the sequence controlling unit 19 judges whether the extracted protocol is a cross-section detecting protocol (step S13). If it is determined that the extracted protocol is not a cross-section detecting protocol (step S13: No), the sequence controlling unit 10 returns to step S11.

On the contrary, if it is determined that the extracted protocol is a cross-section detecting protocol (step S13: Yes), the detecting unit 26b detects (through an automatic detecting process) the cross-sectional position of each of the fourteen types of reference cross-sectional images described above (step S14). Next, the cross-sectional position will be explained. The cross-sectional position denotes, for example, a position indicating a plane in a three-dimensional image space and is expressed by a plurality of parameters.

In the following explanation, the parameters will be referred to as "position parameters". For example, the position parameters are expressed with a center coordinate point o and two unit vectors u and v that are orthogonal to each other, as indicated in Expressions (1) and (2) below.

$$o=(o_x,o_y,o_z) \quad (1)$$

$$u=(u_x,u_y,u_z),v=(v_x,v_y,v_z) \quad (2)$$

Detecting a cross-sectional position denotes calculating the position parameters o, u, and v. The detecting unit 26b stores the detected position parameters of each of the reference cross-sectional images into the storage unit 23. The method for expressing the position parameters is not limited to the example described above. For instance, the position parameters may be expressed in a three-dimensional apparatus space determined by using the center of the magnetic field and the longitudinal direction of the couch of the MRI apparatus 100 as references, instead of the three-dimensional image space. Also, the position parameters may be expressed by using three coordinate points, instead of the center coordinate point and the two unit vectors orthogonal to each other. In other words, any expressing method is acceptable as long as it is possible to uniquely determine the cross-sectional position geometrically.

For example, the detecting unit 26b automatically detects the position of a characteristic site in the multi-slice image, by performing a template matching process with the multi-slice images while using a template of a surrounding image pattern of the characteristic site of the hearts, such as the mitral valve, the tricuspid valve, the aorta valve, the pulmonary valve, the left (right) ventricular apex, the left (right) ventricular outflow tract, and the left (right) ventricular anterior wall, or the like. The detecting unit 26b then calculates the position parameter of each of the reference cross-sectional images on the basis of the detected characteristic sites. In this situation, it is assumed that the template described above is generated in advance prior to the execution of the template matching process. For example, the cross-sectional position of the left ventricular four-chamber long-axis image, which is one of the reference cross-sectional images, is defined as a plane that passes through a position m of the mitral valve, a position t of the tricuspid valve, a position a of the left ventricular apex. In other words, the cross-sectional position of the left ventricular four-chamber long-axis image is defined by the positions of the three points, namely, the position m of the mitral valve, the position t of the tricuspid valve, and the position a of the left ventricular apex. In this situation, when the position m of the mitral valve, the position t of the tricuspid valve, and the position a of the left ventricular apex are expressed as indicated in Expressions (3) below, the position parameters o, u, and v expressing the cross-sectional position of the left ventricular four-chamber long-axis image can be expressed as indicated in Expressions (4) below.

$$m=(m_x,m_y,m_z),t=(t_x,t_y,t_z),a=(a_x,a_y,a_z) \quad (3)$$

$$o=(m+a)/2, v'=a-m, v=v'/|v'|, u'=((t-m)\times v)\times v, u=u'/|u'| \quad (4)$$

In Expressions (4), "(t−m)xv" denotes a cross product of the vector (t−m) and the vector v, whereas "((t−m)xv)xv" denotes a cross product of the vector ((t−m)xv) and the vector v.

Further, the detection of the cross-sectional position of each of the reference cross-sectional images does not necessarily have to be realized by the template matching process. For example, the detecting unit 26b may construct, in advance, a discriminator through a mechanical learning process based on surrounding image patterns of the characteristic sites of the heart and may automatically detect the positions of the characteristic sites in the multi-slice images by using the discriminator. Further, the detecting unit 26b is also able to detect the cross-sectional position of each of the reference cross-sectional images by receiving an input of the positions of the characteristic sites of the heart from the user via the input unit 24. However, because this operation is very complicated and requires time, it is usually preferable to use the method by which the cross-sectional position of each of the reference cross-sectional images is automatically detected. In the first embodiment, for example, there may be some situations where the number of observation-target reference cross-sectional images is smaller than the number of reference cross-sectional images of which the cross-sectional positions are detected. In those situations, by displaying only the observation-target reference cross-sectional images by using the layout information, it is possible to enable the user to easily perform the localizer process on the cross-sectional images.

Subsequently, the display controlling unit 26c obtains the multi-slice images from the storage unit 23 and generates, from the multi-slice images, reference cross-sectional images respectively corresponding to the detected plurality of cross-sectional positions, by performing the MPR process. For example, the display controlling unit 26c generates the fourteen types of reference cross-sectional images (step S15).

After that, the display controlling unit 26c causes the display unit 25 to display the reference cross-sectional images according to the layout indicated by the layout information set with the cross-section detecting protocol (step S16).

The display controlling unit 26c generates a localizer screen in which the reference cross-sectional images that are among the plurality of reference cross-sectional images generated at step S15 and that correspond to the types indicated by the layout information set with the cross-section detecting protocol extracted at step S12 are arranged, in the size indicated by the layout information and in the positional arrangement indicated by the layout, information. The display controlling unit 26c further causes the display unit 25 to display the generated localizer screen. In this situation, the display controlling unit 26c displays reference cross-sectional images on which marks indicating characteristic sites, intersecting lines, and the like are superimposed, over the reference cross-sectional images.

Figure 8:
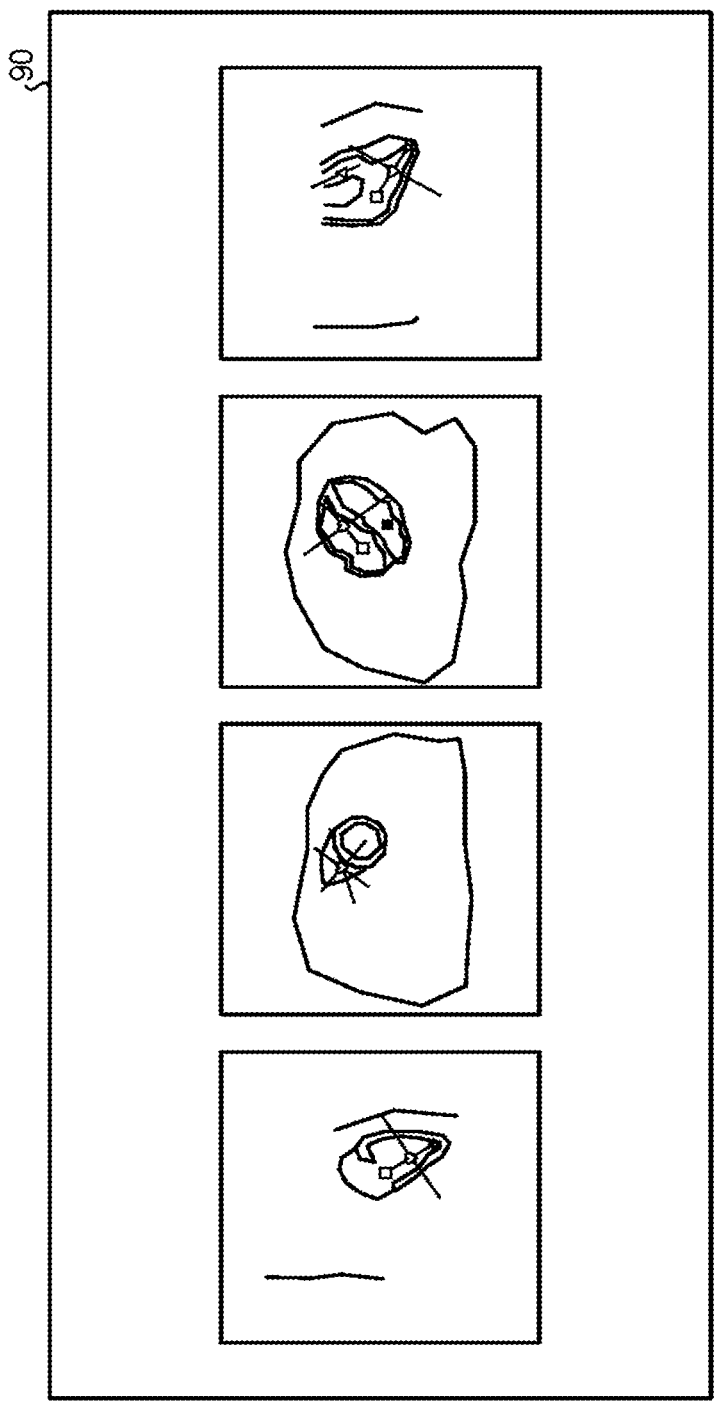
FIG. 8 is a drawing of an example of a screen displayed on a display unit by a display controlling unit according to the first embodiment.

FIG. 8 is a drawing of an example of the localizer screen displayed on the display unit 25 by the display controlling unit 26c according to the first embodiment. For instance, as illustrated by the example in FIG. 8, the display controlling unit 26c causes the display unit 25 to display a localizer screen 90 in which the right ventricular two-chamber long-axis image, the right ventricular short-axis image, the right ventricular four-chamber long-axis image, and the right ventricular three-chamber long-axis image are arranged in a row from the left to the right, in a display area of the display unit 25. As a result, for example, the observation-target reference cross-sectional images are displayed, while the reference cross-sectional images that are not the observation targets are not displayed. It is therefore possible to enable the user to easily observe the observation-target reference cross-sectional images that are considered to be highly relevant to the examination. Consequently, it is possible to enable the user to easily perform the localizer process on the reference cross-sectional images.

Subsequently, the changing unit 26d judges whether a notification (a localizer process completion notification) has been received from the user via the input unit 24, the notification indicating that the localizer process has been completed on the cross-sectional positions of the reference cross-sectional images (step S17). If it is determined that the localizer process completion notification has not been received (step S17: No), the changing unit 26d performs the subsequent process. For example, when the user changes the position of the characteristic site via the input unit 24, the changing unit 26d newly calculates a cross-sectional position by using the post-change position of the characteristic site, with respect to the reference cross-sectional image of which the cross-sectional position is defined by using the post-change position of the characteristic site (step S18). At step S18, also when the position and/or direction of the intersecting line have been changed, the changing unit 26d newly calculates a cross-sectional position by performing a similar process.

For example, the changing unit 26d calculates a three-dimensional position in a three-dimensional image space, on the basis of the post-change two-dimensional position of characteristic site in the reference cross-sectional image in which the change was made to the position of the characteristic site. Further, with respect to another reference cross-sectional image of which the cross-sectional position is defined by using the post-change position of the characteristic site, the changing unit 26d calculates the post-change cross-sectional position by calculating the post-change position parameters while using the same or a similar expression as Expression (4) above, on the basis of the already-calculated three-dimensional position.

After that, the changing unit 26d generates a reference cross-sectional image corresponding to the post-change cross-sectional position, by using the multi-slice images acquired at step S12 and the post-change cross-sectional position and further causes the display unit 25 to display the generated reference cross-sectional image. Subsequently, the changing unit 26d returns to step S17.

On the contrary, when the changing unit 26d determines that the localizer process completion notification has been received (step S17: Yes), the changing unit 26d updates the pre-change cross-sectional position stored in the storage unit 23 with the post-change cross-sectional position (step S19) and returns to step S11.

When it is determined that there is no not-yet-acquired protocol, i.e., when it is determined that the examination should be ended (step S11: Yes), the sequence controlling unit 10 ends the examination.

The MRI apparatus 100 according to the first embodiment has thus been explained. As explained above, the MRI apparatus 100 makes it possible for the user to easily perform the localizer process on the reference cross-sectional images.

Figure 9:
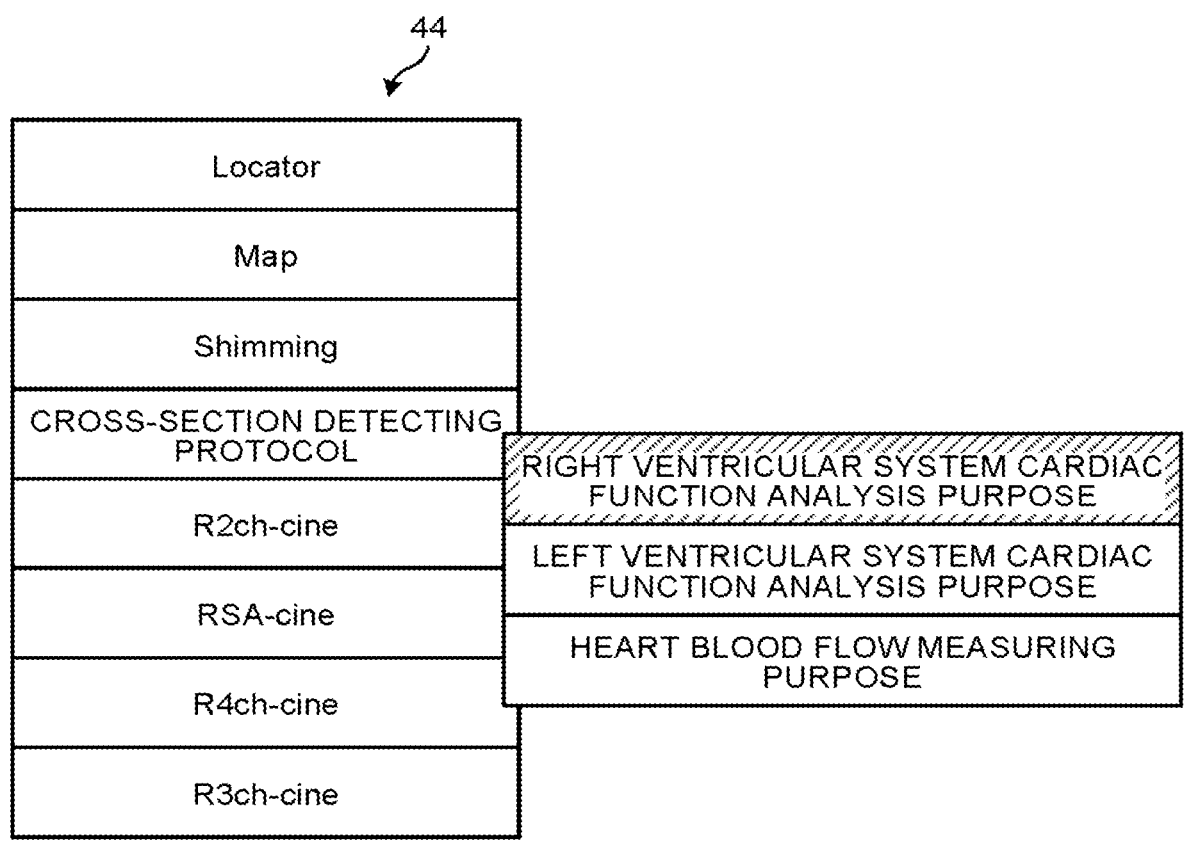
FIG. 9 is a drawing for explaining an example in which a layout kept correspondence with a protocol is changed according to the first embodiment.

In the first embodiment, it is also acceptable to the layout information out with the cross-section detecting protocol, when setting the examination protocols. An example of this situation will be explained, with reference to FIG. 9. FIG. 9 is a drawing for explaining an example in which a layout kept in correspondence with a protocol is changed according to the first embodiment. For example, at step S10 in FIG. 6 explained above, when the user right-clicks on the mouse in the input unit 24, while a cursor (not illustrated) is placed on the name "cross-section detecting protocol" displayed in the area 44, the receiving unit 26a displays a list of all the layout names registered in the layout table 23a, as illustrated by the example in FIG. 9. The example in FIG. 9 indicates that, currently, the cross-section detecting protocol is set with layout information of which the layout name is "right ventricular system cardiac function analysis purpose".

After that, for example, when the user selects the layout name "left ventricular system cardiac function analysis purpose" by operating the input unit 24, the receiving unit 26*a* changes the layout information set with the cross-section detecting protocol displayed in the area 44 to the layout information of which the layout name is "left ventricular system cardiac function analysis purpose" and saves the post-change layout information into the storage unit 23. As explained above, it is possible to change the layout information set with the cross-section detecting protocol, when setting the examination protocols. Consequently, for example, even before the examination is performed, the user is able to easily change the layout information set with the cross-section detecting protocol.

The example is explained above in which the receiving unit 26*a* displays the list of all of the layout names registered in the layout table 23*a* at step S10. However, possible embodiments are not limited to this example. For instance, another arrangement is acceptable in which layout names and layout information are registered in the layout table 23*a* for each user so that, at step S10, the receiving unit 26*a* obtains all of the layout names registered by the user who is currently logged in and displays a list indicating the obtained layout names. In that situation, for example, the possibility that the user may select a piece of layout information other than the pieces of layout information registered by himself/herself is considered to low. The reason is that the layouts indicated by other pieces of layout information may reflect other people's preference and have a high possibility of not reflecting the user's preference. Accordingly, as explained above, by presenting the currently-logged-in user with only the layout names of the pieces of layout information registered by the currently-logged-in user, it is possible to avoid the situation where layout names having a low possibility of being selected are presented in vain.

Further, yet another arrangement is acceptable in which, while layout names and layout information are registered in the layout table 23*a* for each user, the layout table 23*a* further has an item "selection flag". In that situation, when setting examination protocols, the user registers "1" under the item "selection flag" in such record in which the layout information the user desires to have selected is registered under item "layout information". In contrast, the user registers "0" under the item "selection flag" in such a record in which layout information other than the layout information the user desires to have selected is registered under the item "layout information". Further, at step S10, from among the layout names registered by the currently-logged-in user, the receiving unit 26*a* may obtain all of the layout names registered under the item "layout name" in such records that have "1" registered under the item "selection flag", so as to display a list indicating the obtained layout names. For example, by registering "0" under the item "selection flag" for pieces of layout information which have been registered by the user but do not reflect the user's preference and by registering "1" under the item "selection flag" for pieces of layout information reflecting the user's preference, the user is able to have the layout names selected corresponding to the layout information reflecting the user's preference, from among the pieces of layout information registered by the currently-logged-in user. Consequently, it is further possible to avoid the situation where the layout names having a low possibility of being selected are presented in vain. Further, for example, by eliminating from the displayed options such layouts that are already registered but are used less frequently and such layouts that are still under consideration, it is possible to avoid the situation where the layout names having a low possibility of being selected are presented in vain. In addition, for example, preparing selection flags for each user is useful, because it is possible to present only such layout names that reflect each user's preference.

Further, in the first embodiment, the display controlling unit 26*c* may exercise control, at step S16, so as to display characteristic sites and intersecting lines characterizing the reference cross-sectional images corresponding to the types indicated by the layout information and so as not to display other characteristic sites and intersecting lines. The combinations of each of the reference cross-sectional images and characteristic sites and intersecting lines used for defining the cross-sectional position of the reference cross-sectional image are in known relationships. For this reason, the display controlling unit 26*c* is able to control displaying and not displaying the characteristic sites and the intersecting lines by, for example, storing the combinations therein in advance and referring to the combinations when displaying the localizer screen according to the layout information. For instance, in the example of the "right ventricular system cardiac function analysis purpose" described above, the characteristic sites such as the "left ventricular apex" and the "left ventricular outflow tract" are not used for defining the cross-sectional positions of the reference cross-sectional images included in the layout information and are therefore not displayed. It is important, in this manner, not to present the user with redundant information by displaying only such marks that indicate the characteristic sites and the intersecting lines relevant to the types of reference cross-sectional images.

In the description above, the example is explained in which displaying and not displaying are controlled on the basis of the known relationships; however, possible embodiments are not limited to this example. For instance, the display controlling unit 26*c* may receive, from the user, a setting as to which characteristic sites and which intersecting lines should be displayed or should not be displayed.

Further, in the first embodiment, the example is explained in which, at step S1, the user arranges the reference cross-sectional images selected from among the plurality of reference cross-sectional images indicated in the correlation diagram 33*a* into the area 32 by performing the drag-and-drop operation; however, possible embodiments are not limited to this example. For instance, when a layout name is selected from among the list of layout names displayed in the area 31, the receiving unit 26*a* may cause the display unit 25 to display a list of types of reference cross-sectional images in a selectable manner for the user. In that situation, when the user selects one or more types of reference cross-sectional images, the receiving unit 26*a* arranges the reference cross-sectional images corresponding to the type selected by the user in the area 32, sequentially from the left in the predetermined size.

Further, in the first embodiment, on the screen 30 displayed at step S1, when the user has arranged a reference cross-sectional images in the area 32, the receiving unit 26*a* may cause the display unit 25 to display a message that prompts the user to arrange another reference cross-sectional image. For example, when the right ventricular three-chamber long-axis image has been arranged in the area 32, the receiving unit 26*a* displays a message "arranging the RSA is recommended" in the vicinity of the area 32, so as to prompt the user to arrange the right ventricular short-axis image, because it is easy to check the cross-sectional position in the right ventricular short-axis image, which is positioned close in the correlation diagram 33a. By using the message in a pinpoint manner as described above and presenting the user with the reference cross-sectional image to be used when reference cross-sectional images are set manually, it is possible to enable the user to easily generate a layout in which a reference cross-sectional image is displayed together with another reference cross-sectional image that is set immediately prior to the reference cross-sectional image. Further, when a reference cross-sectional image has been arranged in the area 32, the receiving unit 26a may apply an emphasis (e.g., with a highlight) to the display of another reference cross-sectional image that is among the plurality of reference cross-sectional images indicated in the correlation diagram 33a and is set immediately prior to the arranged reference cross-sectional image. In the first embodiment, the example is explained in which the correlation diagram 33a indicates the general procedure for manually setting the reference cross-sectional images; however, possible embodiments are not limited to this example. The correlation diagram 33a may be generated according to an arbitrary policy. For example, the correlation diagram 33a may express a relationship between a reference cross-sectional image and another reference cross-sectional image that makes it easier to check the cross-sectional position of the reference cross-sectional image.

Further, in the first embodiment, the example is explained in which one piece of layout information is set with the cross-section detecting protocol; however, possible embodiments are not limited to this example. For instance, a plurality of pieces of layout information may be set with the cross-section detecting protocol. Next, an example will be explained in which as many pieces of layout information as N (where N is a natural number of 2 or larger) are set with the cross-section detecting protocol. In that situation, at step S16, the display controlling unit 26c displays, in each of N sectional areas into which the localizer screen is divided, a reference cross-sectional image according to the layout indicated by a corresponding one of the pieces of layout information. In other words, the display controlling unit 26c is able to display, on the localizer screen, the reference cross-sectional images according to the layouts indicated by the N pieces of layout information, from among the reference cross-sectional images corresponding to the cross-sectional positions detected by the detecting unit 26b. As a result, for example, when one examination has a plurality of purposes, it is possible to display reference cross-sectional images corresponding to the plurality of purposes, by setting the cross-section detecting protocol with the layout information corresponding to each of the plurality of purposes.

Second Embodiment

In the description of the MRI apparatus 100 according to the first embodiment above, the example is explained in which the user manually sets the layout information with the cross-section detecting protocol, for each of the different types of examinations; however possible embodiments are not limited to this example. For instance, an MRI apparatus may automatically generate layout information corresponding to each of different types of examinations. An example will be explained as a second embodiment.

An MRI apparatus according to the second embodiment does not perform the process of registering the layout information indicated in FIG. 3 in the first embodiment. Further, the MRI apparatus according to the second embodiment performs various types of processes (e.g., the various types of processes at steps S30 to S40 explained later) to automatically generate the layout information, instead of the process at step S16 in the first embodiment. Some of the configurations that are the same as those in the first embodiment will be referred to by using the same reference characters, and the explanation thereof will be omitted.

Figure 10:
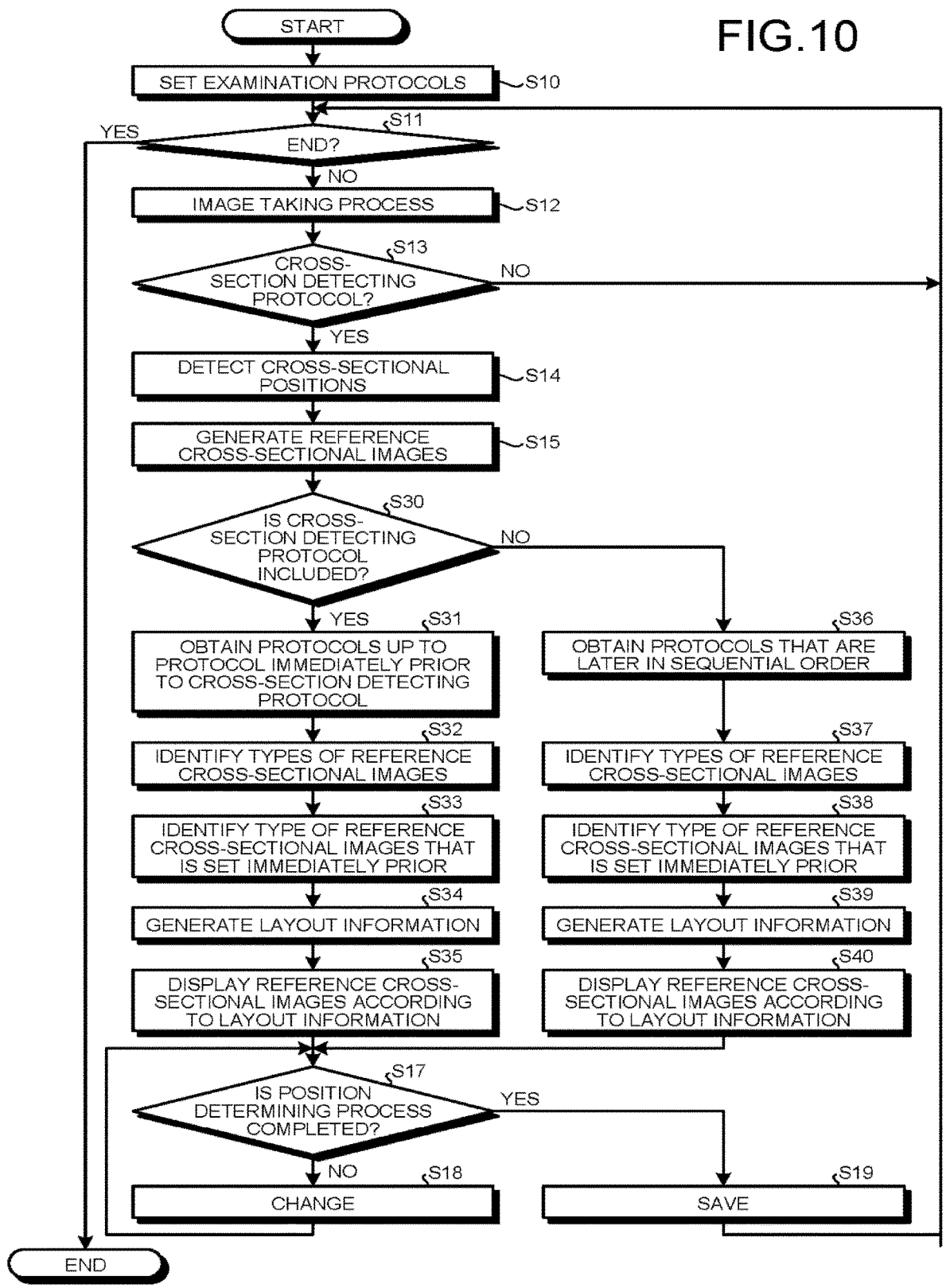
FIG. 10 is a flowchart of a processing procedure performed when a medical examination is performed according to the second embodiment.

A flow in a process performed by the MRI apparatus according to the second embodiment when performing an examination will be explained. FIG. 10 is a flowchart of a processing procedure performed when an examination is performed according to the second embodiment.

Figure 11:
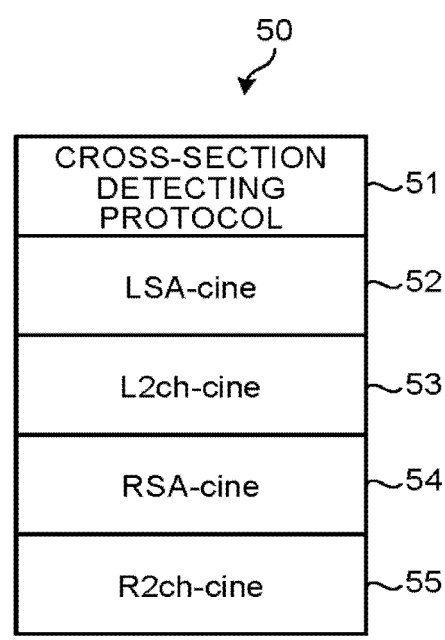
FIG. 11 is a drawing of examples of examination protocols according to the second embodiment.
Figure 12:
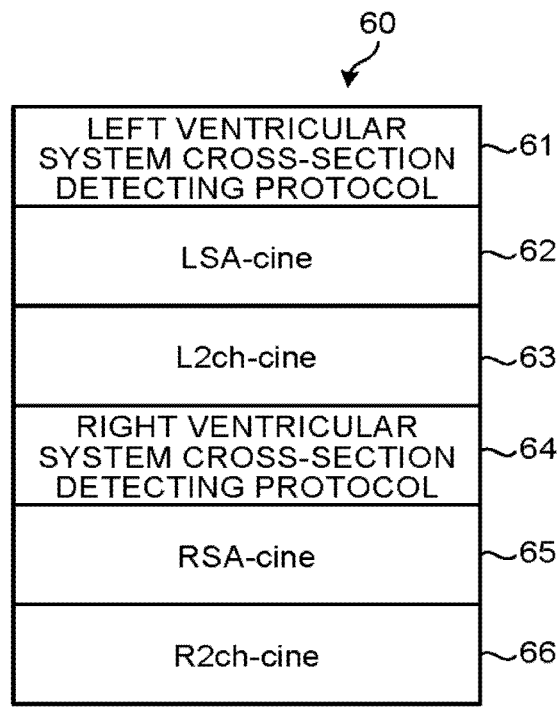
FIG. 12 is a drawing of more examples of examination protocols according to the second embodiment.

As illustrated by the example in FIG. 10, the processes at steps S10 to S15 and S17 to S19 are the same as those in the first embodiment. Thus, the explanation thereof will be omitted. FIGS. 11 and 12 are drawings of examples of examination protocols according to the second embodiment. For example, at step S10, examination protocols 50 in the example of FIG. 11 or examination protocols 60 in the example of FIG. 12 are set.

The examination protocols 50 include the first protocol (a cross-section detecting protocol) 51, the second protocol 52 named "LSA-cine", the third protocol 53 named "L2ch-cine", the fourth protocol ("RSA-cine") 54, and the fifth protocol ("R2ch-cine") 55. Of these protocols 51 to 55, the contents of the protocols 51, 54, and 55 are the same as described above. "LSA-cine" is the name of a protocol defining various types of image taking conditions and the like to acquire the left ventricular short-axis image through a cine imaging process. Further, "L2ch-cine" is the name of a protocol defining various types of image taking conditions and the like to acquire the left ventricular two-chamber long-axis image through a cine imaging process. In the following explanations, the protocol named "LSA-cine" and the protocol named "L2ch-cine" will simply be referred to as "LSA-cine" and "L2ch-cine", respectively.

Further, the examination protocols 60 include the first protocol 61 named "left ventricular system cross-section detecting protocol", the second protocol ("LSA-cine") 62, the third protocol ("L2ch-cine") 63, the fourth protocol 64 named "right ventricular system cross-section detecting protocol", the fifth protocol ("RSA-cine") 65, and the sixth protocol ("R2ch-cine") 66. Of these protocols 61 to 66, the contents of the protocols 62, 63, 65, and 66 are the same as described above. The protocol 61 is a protocol defining various types of conditions to acquire multi-slice images and various types of conditions to detect the cross-sectional positions of seven types of reference cross-sectional images by using the multi-slice images. In this situation, the seven types of reference cross-sectional images are, for example, seven reference cross-sectional images of which the types are a left ventricular vertical long-axis image, a left ventricular horizontal long-axis image, a left ventricular short-axis image, a left ventricular two-chamber long-axis image, a left ventricular three-chamber long-axis image, a left ventricular four-chamber long-axis image, and a left ventricular outflow tract image. Further, the protocol 64 is a protocol defining various types of conditions to acquire multi-slice images and various types of conditions to detect the cross-sectional positions of five types of reference cross-sectional images by using the multi-slice images. In this situation, the five types of reference cross-sectional images are, for example, five reference cross-sectional images of which the types are a right ventricular short-axis image, a right ventricular two-chamber long-axis image, a right ventricular three-chamber long-axis image, a right ventricular four-chamber long-axis image, and a right ventricular outflow tract image.

In the second embodiment, the protocol 61 and the protocol 64 are treated in the same manner as the "cross-section detecting protocol". For example, when the protocol 61 or the protocol 64 is extracted at step S12, the sequence controlling unit 10 determines that the extracted protocol 61 or 64 is a cross-section detecting protocol at step S13.

After that, in the second embodiment, at step S30, the display controlling unit 26c judges, with respect to the examination protocols set at step S10, whether the protocols that are later in the sequential order than the protocol extracted at step S12 include a cross-section detecting protocol (step S30).

For example, when the examination protocols 50 are set at step S10, and the protocol 51 is extracted at step S12, the display controlling unit 26c determines that no cross-section detecting protocol is included in the protocols 52 to 55 that are later in the sequential order than the protocol 51. In another example, when the examination protocols 60 are set at step S10, and the protocol 61 is extracted at step S12, the display controlling unit 26c determines that the protocol 64 is included as a cross-section detecting protocol in the protocols 62 to 65 that are later in the sequential order than the protocol 61.

When it is determined that a cross-section detecting protocol is included (step S30: Yes), the display controlling unit 26c obtains the protocols starting with the protocol immediately subsequent to the protocol extracted at step S12 up to the protocol immediately prior to the cross-section detecting protocol determined to be included at step S30 (step S31).

After that, the display controlling unit 26c identifies the types of reference cross-sectional images to be acquired by the imaging scan performed according to the obtained protocol (step S32). Subsequently, the display controlling unit 26c refers to the correlation diagram 33a stored in the storage unit 23 and identifies the type of the reference cross-sectional image that is, when reference cross-sectional images are set manually, set immediately prior to the reference cross-sectional image of which the type was identified at step S32 (step S33). The process at step S33 may be omitted.

After that, the display controlling unit 26c generates layout information indicating a layout in which the reference cross-sectional images corresponding to the types identified at steps S32 and S33 are arranged in a row from the left to the right in the predetermined size (step S34).

Subsequently, the display controlling unit 26c causes the display unit 25 to display the reference cross-sectional images that are among the plurality of types of reference cross-sectional images generated at step S15 and that correspond to the types indicated by the layout information generated at step S34, in the size and the positional arrangement indicated by the layout information (step S35). After that, the display controlling unit 26c proceeds to step S17.

Figure 13:
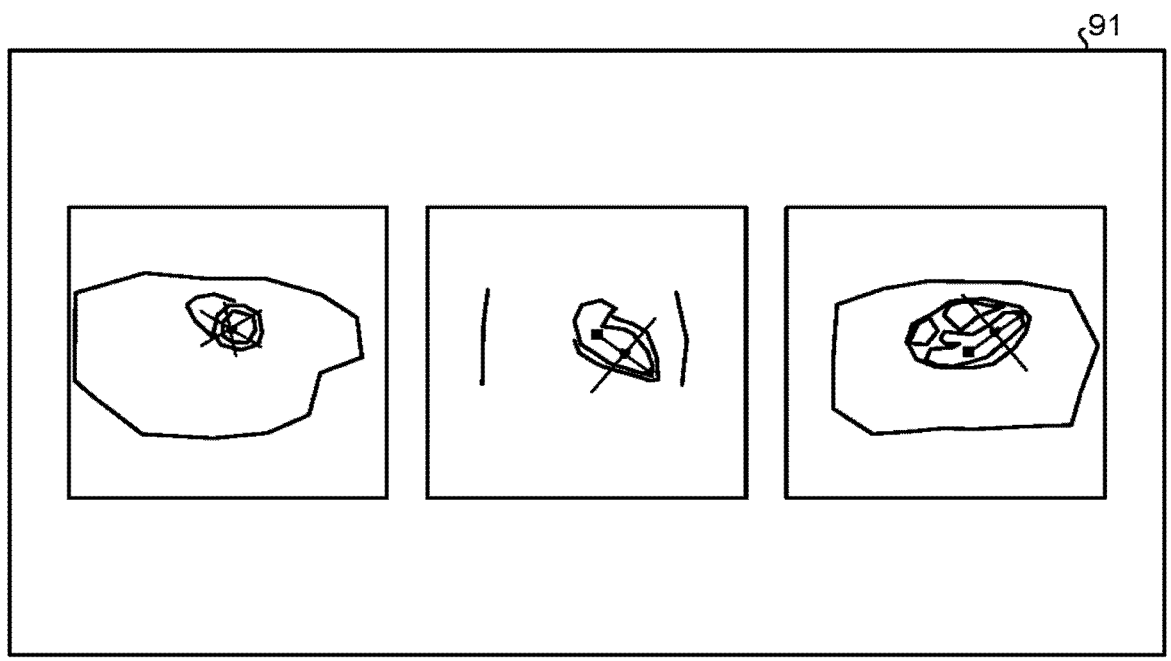
FIG. 13 is a drawing of an example of a localizer screen displayed on a display unit according to the second embodiment.

For example, when it is determined at step S30 that the protocol 64 is included as a cross-section detecting protocol, the display controlling unit 26c obtains the protocols starting with the protocol 62 up to the protocol 63 at step S31. After that, at step S32, the display controlling unit 26c identifies the type "left ventricular short-axis image" corresponding to the reference cross-sectional image acquired by the imaging scan performed according to the protocol 62 and the type "left ventricular two-chamber long-axis image" corresponding to the reference cross-sectional image acquired by the imaging scan performed according to the protocol 63. Subsequently, at step S33, the display controlling unit 26c refers to the correlation diagram 33a and identifies the type "left ventricular horizontal long-axis image" of reference cross-sectional image that is set immediately prior to the reference cross-sectional image corresponding to the type "left ventricular short-axis image" and identifies the type "left ventricular short-axis image" of reference cross-sectional image that is set immediately prior to the reference cross-sectional image corresponding to the type "left ventricular two-chamber long-axis image". Subsequently, at step S34, the display controlling unit 26c generates layout information indicating a layout in which the plurality of reference cross-sectional images corresponding to the types "left ventricular short-axis image", "left ventricular two-chamber long-axis image", and "left ventricular horizontal long-axis image" are arranged in a row from the left to the right in the predetermined size. FIG. 13 is a drawing of an example of a localizer screen 91 displayed on the display unit 25 according to the second embodiment. Further, at step S35, the display controlling unit 26c causes the display unit 25 to display, as illustrated by the example in FIG. 13, the reference cross-sectional images (the plurality of reference cross-sectional images corresponding to the types "left ventricular short-axis image", "left ventricular two-chamber long-axis image", and "left ventricular horizontal long-axis image") that are among the seven types of reference cross-sectional images described above and that correspond t the types indicated by the layout information generated at step S34, in the predetermined size and the positional arrangement indicated by the layout information.

At step S34, the display controlling unit 26c is able to generate the layout information indicating the layout that enables the user to understand that the two reference cross-sectional images correspond to each other, by arranging, in a row, the one reference cross-sectional image together with the other reference cross-sectional image that is set immediately prior to the one reference cross-sectional image when reference cross-sectional images are set manually. In this situation, "the one reference cross-sectional image" may be referred to s a "child", whereas "the other reference cross-sectional image that is set immediately prior to the one reference cross-sectional image" may be referred to as a "parent". Further, the relationship between "the one reference cross-sectional image" and "the other reference cross-sectional image that is set immediately prior to the one reference cross-sectional image" may be referred to as a "parent-child relationship". In other words, at step S34, the display controlling unit 26c is able to generate the layout information in which the two reference cross-sectional images that are in the "parent-child" relationship are arranged in a row.

Figure 14:
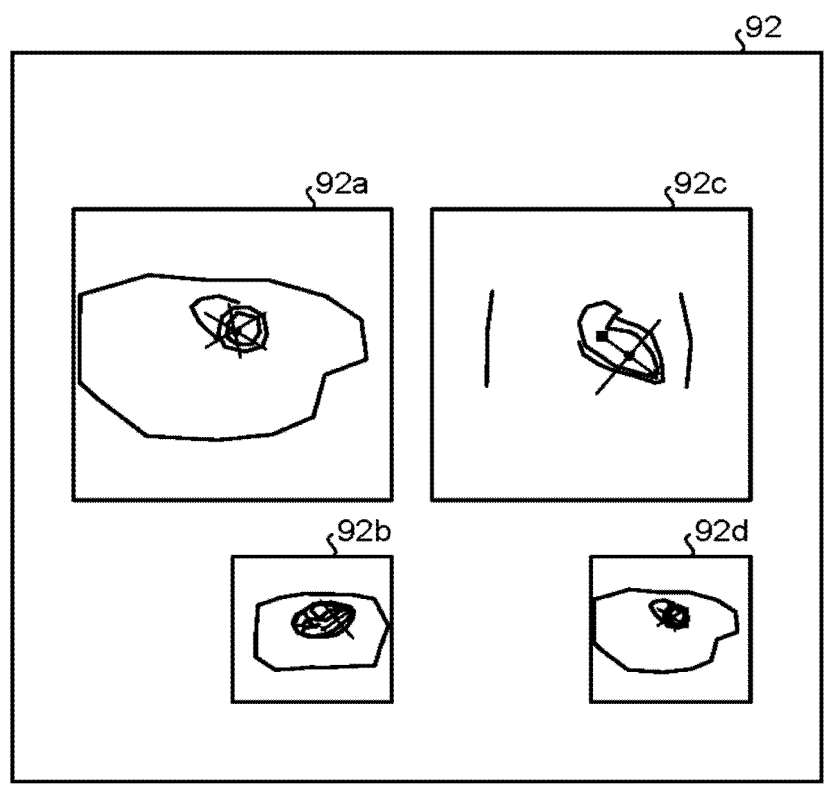
FIG. 14 is a drawing of an example of another localizer screen displayed on the display unit according to the second embodiment.

FIG. 14 is a drawing of an example a localizer screen 92 displayed on the display unit 25 according to the second embodiment. For instance, an example will be explained in which the types "left ventricular short-axis image" and "left ventricular two-chamber long-axis image" are identified at step S32, and subsequently at step S33, the type "left ventricular horizontal long-axis image" of the reference cross-sectional image serving as a "parent" of the reference cross-sectional image corresponding to the type "left ventricular short-axis image" serving as a "child" as well as the type "left ventricular short-axis" of the reference cross-sectional image serving as a "parent" of the reference cross-sectional image corresponding to the type "left ventricular two-chamber long-axis image" serving as a "child" are identified.

In that situation, as indicated by the example in FIG. 14, the display controlling unit 26c generates layout information indicating a layout in which a reference cross-sectional image 92*a* corresponding to the type "left ventricular short-axis image" identified at step S32 and serving as a "child" and another reference cross-sectional image 92*b* corresponding to the type "left ventricular horizontal long-axis image" and serving as a "parent" of the "child" are arranged in an up-and-down direction so as to correspond to each other; and in which a reference cross-sectional image 92*c* corresponding to the type "left ventricular two-chamber long-axis image" identified at step S32 and serving as a "child" and another reference cross-sectional image 92*d* corresponding to the type "left ventricular two-chamber long-axis image" and serving as a "parent" of the "child" are arranged in an up-and-down direction so as to correspond to each other, while the sizes of the reference cross-sectional image 92*a* and the reference cross-sectional image 92*c* each serving as a "child" are larger than the sizes of the reference cross-sectional image 92*b* and the reference cross-sectional image 92*d* each serving as a "parent". In this situation, the reason why the sizes of the "child" reference cross-sectional images are larger than the sizes of the "parent" reference cross-sectional images is that the "parent" reference cross-sectional images are only information-purpose reference cross-sectional images, whereas the "child" reference cross-sectional images are important reference cross-sectional images serving as the observation targets. Further, at step S35, the display controlling unit 26*c* displays, as illustrated by the example in FIG. 14, the reference cross-sectional images 92*a* to 92*d* on the localizer screen 92, according to the layout information generated at step S34. It is effective in checking the positions of the observation-target reference cross-sectional images to display, in this manner, the reference cross-sectional image together that is close, in the manual setting procedure, to each of the observation-target reference cross-sectional images on the localizer screen, even if the reference cross-sectional image is not an observation target. With reference to FIG. 14, the example is explained in which the sizes of the "child" reference cross-sectional images are larger than the "parent" reference cross-sectional images; however, possible embodiments are not limited to this example. For instance, on the contrary, the sizes of the "parent" reference cross-sectional images may be larger than the sizes of the "child" reference cross-sectional images. The "parent" reference cross-sectional images are referred to, when setting the cross-sectional positions of the "child" reference cross-sectional images, which are important reference cross-sectional images as the observation targets. Accordingly, from the aspect of precisely fine-tuning the positions of the characteristic sites and the intersecting lines in the "parent" reference cross-sectional images, it is more convenient when the sizes of the "parent" reference cross-sectional images are larger than the sizes of the "child" reference cross-sectional images.

Returning to the description of FIG. 10, when it is determined, on the contrary, that no cross-section detecting protocol is included (step S30: No), the display controlling unit 26*c* obtains all the protocols that are later, in the sequential order, than the protocol extracted at step S12 (step S36).

After that, the display controlling unit 26*c* identifies the types of reference cross-sectional images generated according to the obtained protocols (step S37).

Subsequently, the display controlling unit 26*c* refers to the correlation diagram 33*a* and identifies the type of the reference cross-sectional image that is, when reference cross-sectional images are set manually, set immediately prior to the reference cross-sectional image of which the type was identified at step S37 (step S38). The process at step S38 may be omitted.

After that, the display controlling unit 26*c* generates layout information indicating a layout in which the reference cross-sectional images corresponding to the types identified at steps S37 and S38 are arranged in a row from the left to the right in the predetermined size (step S39).

After that, the display controlling unit 26*c* causes the display unit 25 to display the reference cross-sectional images that are among the plurality of types of reference cross-sectional images generated at step S15 and that correspond to the types indicated by the layout information generated at step S39, in the size and the positional arrangement indicated by the layout information (step S40). Subsequently, the display controlling unit 26*c* proceeds to step S17.

For example, when the examination protocols 50 are set at step S10, the display controlling unit 26*c* determines at step S30 that no cross-section detecting protocol is included. After that, at step S36, the display controlling unit 26*c* obtains the protocols 52 to 55 that are later, in the sequential order, than the protocol 51. Subsequently, at step S37, the display controlling unit 26*c* identifies the type "left ventricular short-axis image" corresponding to the reference cross-sectional image acquired by the imaging scan performed according to the protocol 52, the type "left ventricular two-chamber long-axis image" corresponding to the reference cross-sectional image acquired by the imaging scan performed according to the protocol 53, the type "right ventricular short-axis image" corresponding to the reference cross-sectional image acquired by the imaging scan performed according to the protocol 54, and the type "right ventricular two-chamber long-axis image" corresponding to the reference cross-sectional image acquired by the imaging scan performed according to the protocol 55.

After that, at step S38, the display controlling unit 26*c* refers to the correlation diagram 33*a* and identifies the type "left ventricular horizontal long-axis image" corresponding to the reference cross-sectional image that is set immediately prior to the reference cross-sectional image corresponding to the type "left ventricular short-axis image". Also, at step S38, the display controlling unit 26*c* identifies the type "left ventricular short-axis image" corresponding to the reference cross-sectional image that is set immediately prior to the reference cross-sectional image corresponding to the type "left ventricular two-chamber long-axis image". In addition, at step S38, the display controlling unit 26*c* identifies the type "right ventricular two-chamber long-axis image" corresponding to the reference cross-sectional image that is set immediately prior to the reference cross-sectional image corresponding to the type "right ventricular short-axis image". Furthermore, at step S38, the display controlling unit 26*c* identifies the type "left ventricular four-chamber long-axis image" corresponding to the reference cross-sectional image that is set immediately prior to the reference cross-sectional image corresponding to the type "right ventricular two-chamber long-axis image".

Figure 15:
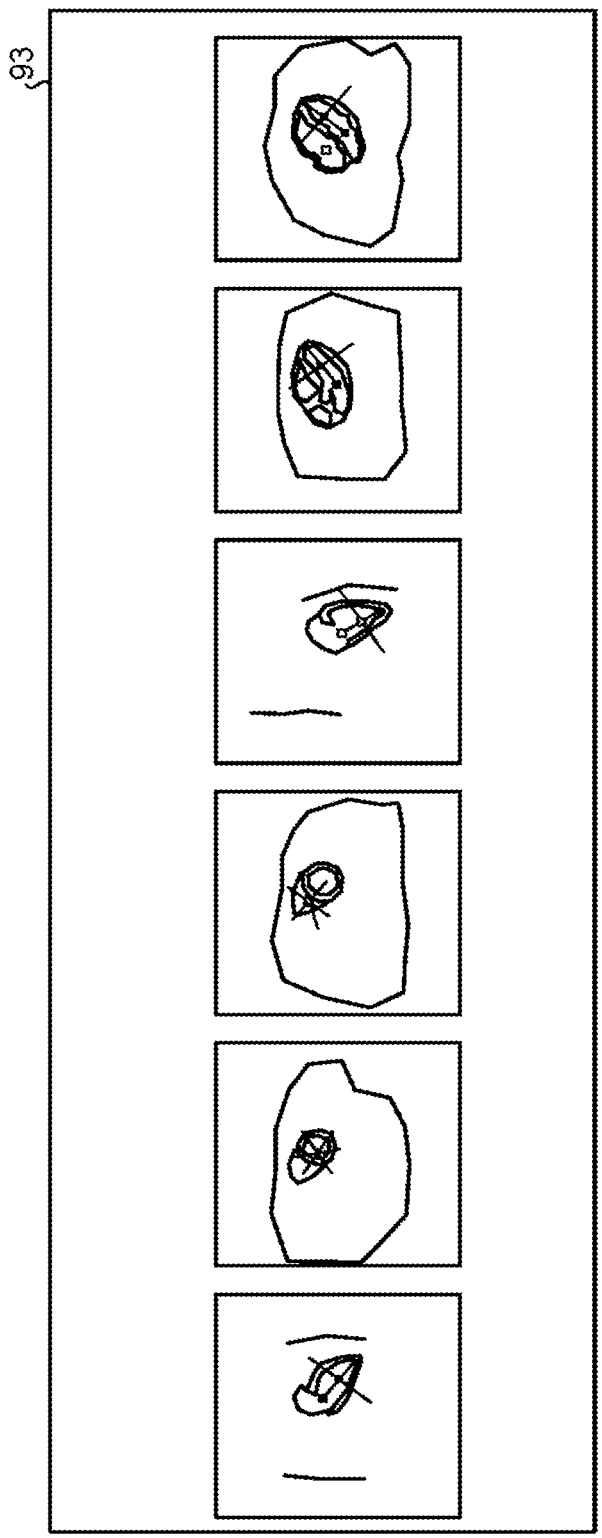
FIG. 15 is a drawing of an example of yet another localizer screen displayed on the display unit according to the second embodiment.

After that, at step S39, the display controlling unit 26*c* generates layout information indicating a layout in which a plurality of reference cross-sectional images corresponding to the types "left-ventricular two-chamber long-axis image", "left ventricular short-axis image", "right ventricular short-axis image", "right ventricular two-chamber long-axis image", "left ventricular horizontal long-axis image", and "left ventricular four-chamber long-axis image" are arranged in a row from the left to the right in the predetermined size. FIG. 15 is a drawing of an example of yet another localizer screen 93 displayed on the display unit 25 according to the second embodiment. Subsequently, at step S40, as illustrated by the example in FIG. 15, the display controlling unit 26c displays, on the localizer screen 93, reference cross-sectional images (a plurality of reference cross-sectional images corresponding to the types "left ventricular two-chamber long-axis image", "left ventricular short-axis image", "right ventricular short-axis image", "right ventricular two-chamber long-axis image", "left ventricular horizontal long-axis image", and "left ventricular four-chamber long-axis image") that are among the fourteen types of reference cross-sectional images generated at step S15 and that correspond to the types indicated by the layout information generated at step S39, in the predetermined size and the positional arrangement indicated by the layout information.

Figure 16:
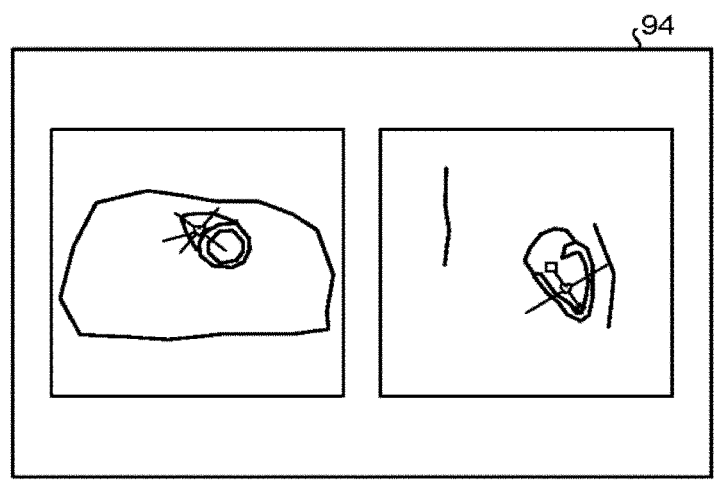
FIG. 16 is a drawing of an example of yet another localizer screen displayed on the display unit according to the second embodiment.

Next, an example in which the protocol 64 is extracted at step S12 will be explained. In that situation, the display controlling unit 26c determines at step S30 that no cross-section detecting protocol is included. Further, at step S36, the display controlling unit 26c obtains the protocols 65 and 66 that are later, in the sequential order, than the protocol 64. After that, at step S37, the display controlling unit 26c identifies the type "right ventricular short-axis image" corresponding to the reference cross-sectional image acquired by the imaging scan performed according to the protocol 65 and the type "right ventricular two-chamber long-axis image" corresponding to the reference cross-sectional image acquired by the imaging scan performed according to the protocol 66. Subsequently, at step S38, the display controlling unit 26c refers to the correlation diagram 33a and identifies the type "right ventricular two-chamber long-axis, image" corresponding to the reference cross-sectional image that is set immediately prior to the reference cross-sectional image corresponding to the type "right ventricular short-axis image". Further, at step S38, the display controlling unit 26c identifies the type "left ventricular four-chamber long-axis image" corresponding to the reference cross-sectional image that is set immediately prior to the reference cross-sectional image corresponding to the type "right ventricular two-chamber long-axis image". Subsequently, at step S39, the display controlling unit 26c generates layout information indicating a layout in which a plurality of reference cross-sectional images corresponding to the types "right ventricular short-axis image" and "right ventricular two-chamber long-axis image" (excluding the "left ventricular four-chamber long-axis image") are arranged in a row from the left to the right in the predetermined size. FIG. 16 is a drawing of an example of yet another localizer screen 94 displayed on the display unit 25 according to the second embodiment. Subsequently, at step S40, as illustrated by the example in FIG. 16, the display controlling unit 26c displays, on the localizer screen 94, reference cross-sectional images (a plurality of reference cross-sectional images corresponding to the types "right ventricular short-axis image" and "right ventricular two-chamber long-axis image") that are among the five types of reference cross-sectional images and that correspond to the types indicated by the layout information generated at step S39, in the predetermined size and the positional arrangement indicated by the layout information.

At one or both of steps S35 and S40, the display controlling unit 26c may also offer a means for checking, in a simple manner, the layout of the reference cross-sectional images to the user before displaying the localizer screen. For example, the display controlling unit 26c may cause the display unit 25 to also display a thumbnail in which the reference cross-sectional images are arranged in a row. In that situation, the user checks the thumbnail and if the layout of the reference cross-sectional images does not reflect the user's preference, the user inputs an instruction by operating the input unit 24, so as to cause the display unit 25 to display the receiving screen described above that receives editing of the layout information. When the instruction is input, the receiving unit 26a causes the display unit 25 to display the receiving screen. As a result, the user is able to edit the layout information on the receiving screen.

Further, at one or both of steps S35 and S40, the display controlling unit 26c may also receive an instruction to cause the display unit 25 to display the receiving screen after displaying the localizer screen. As a result, when the layout of the reference cross-sectional images on the localizer screen does not reflect the user's preference, the user is able to input an instruction to cause the receiving screen to be displayed and to edit the layout information on the displayed receiving screen.

The MRI apparatus according to the second embodiment has thus been explained. The MRI apparatus according to the second embodiment automatically generates the layout information indicating the layout in which the types of reference cross-sectional images acquired by the imaging scans are arranged in a row from the left to the right in the predetermined size and causes the display unit 25 to display the reference cross-sectional images according to the generated layout information. Accordingly, because the MRI apparatus according to the second embodiment does not display any reference cross-sectional images that are not the observation targets, it is possible to reduce the burden on the user when he/she performs the localizer process on the reference cross-sectional images. Consequently, the MRI apparatus according to the second embodiment makes it possible for the user to even more easily perform the localizer process on the reference cross-sectional images.

First Modification Example of Second Embodiment

In the second embodiment, the example is explained in which, with respect to the examination protocol that are set, the MRI apparatus identifies the types of reference cross-sectional images to be acquired by the imaging scans performed either according to all the protocols including and following the protocol immediately subsequent to a certain cross-section detecting protocol or according to the protocols starting with the protocol immediately subsequent to a certain cross-section detecting protocol up to the protocol immediately prior to the next cross-section detecting protocol; however, possible embodiments are not limited to this example. For instance, for some of the protocols with which imaging scans have already been performed, because reference cross-sectional images have already been acquired in the imaging scans, it may not be necessary to display, for the localizer purposes, the reference cross-sectional images acquired by the imaging scans performed according to the protocols. For this reason, the MRI apparatus may be configured so as not to display the reference cross-sectional images corresponding to the types acquired according to the protocols with which imaging scans have already been performed.

In other words, with respect to the examination protocols that are set, the MRI apparatus may identify the types of reference cross-sectional images to be acquired by the imaging scans performed either according to all the protocols including and following the protocol immediately subsequent to a certain cross-section detecting protocol or according to the protocols starting with the protocol immediately subsequent to a certain cross-section detecting protocol up to the protocol immediately prior to the next cross-section detecting protocol from which the protocols with which imaging scan have already been performed are excluded. An example will be explained as a first modification example of the second embodiment.

Figure 17:
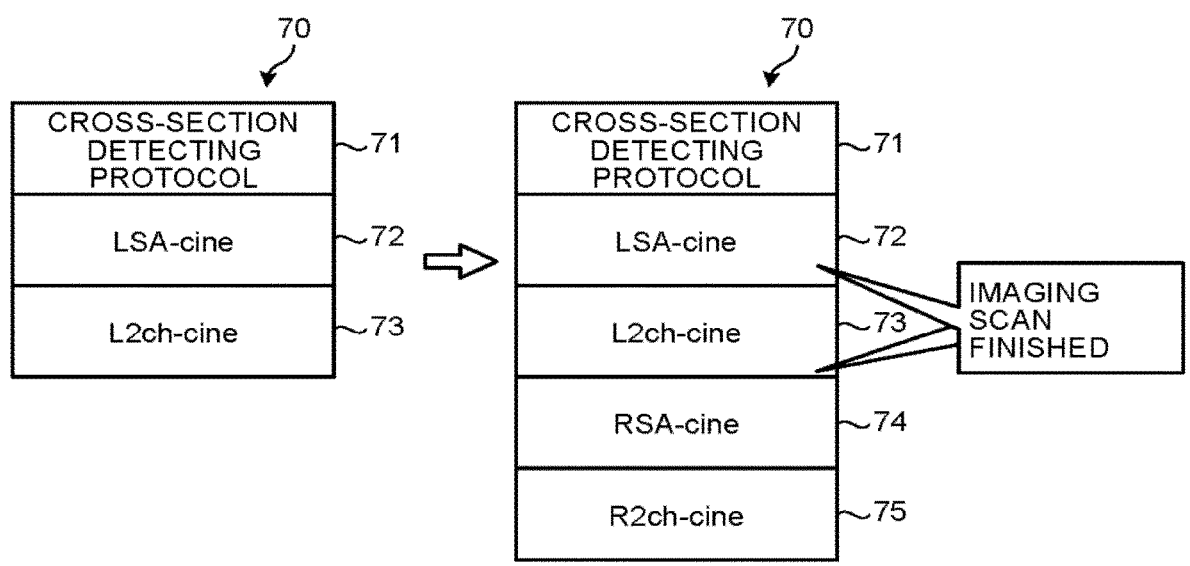
FIG. 17 is a drawing of examples before and after a change is made to examination protocols according to a first modification example of the second embodiment.

FIG. 17 is a drawing of examples before and after a change is made to examination protocols 70 according to the first modification example of the second embodiment. For instance, as illustrated by the example in FIG. 17, the examination protocols 70 before the change (hereinafter, "pre-change protocols") include the first protocol (a cross-section detecting protocol) 71, the second protocol ("LSA-cine") 72, and the third protocol ("L2ch-cine") 73.

In this situation, an example will be explained in which, after an MRI apparatus according to the first modification example performs various types of processes according to all of the protocols 71 to 73 included in the pre-change examination protocols 70, the user makes a change to newly add the fourth protocol ("RSA-cine") 74 and the fifth protocol ("R2ch-cine") 75 to the examination protocols 70, and the examination protocols 70 are subsequently implemented again.

In that situation, the MRI apparatus performs various types of processes according to the protocols 71 to 75 included in the examination protocols 70 after the change (hereinafter, "post-change examination protocols"). For example, when performing a process according to the protocol 71, the display controlling unit 26c included in the MRI apparatus according to the first modification example identifies the types of reference cross-sectional images acquired by the imaging scans performed according to the protocols 74 and 75, by excluding the protocols 71 and 72 with which imaging scans have already been performed, from the protocols 72 to 75. After that, the display controlling unit 26c refers to the correlation diagram 33a and identifies the type of reference cross-sectional image that is set immediately prior to the reference cross-sectional image of which the type was identified. Subsequently, the display controlling unit 26c generates layout information indicating a layout in which the reference cross-sectional images corresponding to the identified types are arranged in a row from the left to the right in the predetermined size. After that, the display controlling unit 26c displays the reference cross-sectional images that are among the plurality of reference cross-sectional images generated at step S15 and that correspond to the types indicated by the layout information, in the size and the positional arrangement indicated by the layout information.

As explained above, the display controlling unit 26c causes the display unit 25 to display the types of reference cross-sectional images acquired by the not-yet-performed imaging scans. Accordingly, when the MRI apparatus according to the first modification example of the second embodiment is used, the display unit 25 will not display such reference cross-sectional images that may not be required by the localizer process of the reference cross-sectional images, such as the reference cross-sectional images acquired according to the protocols 71 and 72 with which the imaging scans have already been performed. Consequently, the MRI apparatus according to the first modification example of the second embodiment makes it possible for the user to perform the localizer process on the reference cross-sectional images even more easily.

Second Modification Example of Second Embodiment

Next, an example will be explained in which, an MRI apparatus performs an imaging scan according to a protocol, and during the time period between when the imaging scan is completed and when an imaging scan is performed according to the subsequent protocol, the MRI apparatus receives an instruction to perform a process according to a cross-section detecting protocol from the user via the input, unit 24. In other words, the example will be explained in which the cross-section detecting protocol is set between any two of the plurality of protocols included in the examination protocols. In that situation, the MRI apparatus performs the process according to the cross-section detecting protocol that was set, on the basis of the received instruction. An example in this situation will be explained as a second modification example of the second embodiment. Further, the cross-section detecting protocol is one case of the a protocol defining an image taking condition for performing a predetermined process.

Figure 18:
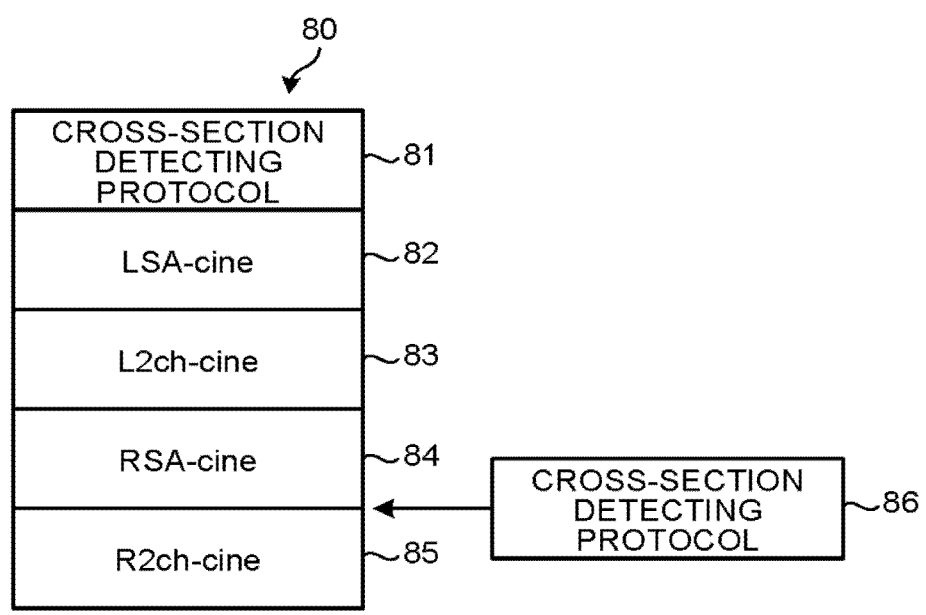
FIG. 18 is a drawing of an example of examination protocols according to a second modification example of the second embodiment.

FIG. 18 is a drawing of an example of examination protocols 80 according to the second modification example of the second embodiment. As indicated by the example in FIG. 18, the examination protocols 80 include a first protocol (a cross-section detecting protocol) 81, a second protocol ("LSA-cine") 82, a third protocol ("L2ch-cine") 83, a fourth protocol ("RSA-cine") 84, and a fifth protocol ("R2ch-cine") 85.

When performing an examination, an MRI apparatus according to the second modification example performs various types of processes according to the protocols 81 to 84 included in the examination protocols 80. In this situation, an example will be explained in which an instruction is input by the user via the input unit 24 to perform a process according to a cross-section detecting protocol 86, after the process according to the protocol 84 is completed, but before the process according to the protocol 85 is started. As a result of the instruction, the cross-section detecting protocol 86 is set between the protocol 84 and the protocol 65.

In that situation, the display controlling unit 26c performs the process according to the cross-section detecting protocol 86, after the process according to the protocol 84 is completed, but before the process according to the protocol 85 is performed. In the present example, because the fourteen types of cross-sectional positions have already been detected, the display controlling unit 26c does not newly detect the fourteen types of cross-sectional positions. Further, the display controlling unit 26c performs the same process as described in the second embodiment or the first modification example, by using the already-detected cross-sectional positions. For example, the display controlling unit 26c identifies the types of reference cross-sectional images acquired by the imaging scan performed according to the protocol 85. After that, the display controlling unit 26c refers to the correlation diagram 33a and identifies the type of the reference cross-sectional image that is set immediately prior to the reference cross-sectional image of which the type was identified. Subsequently, the display controlling unit 26c generates layout information indicating a layout in which the reference cross-sectional images corresponding to the specified types are arranged in a row from the left to the right in the predetermined size. After that, the display controlling unit 26c displays the reference cross-sectional images that are among the generated plurality of reference cross-sectional images and that correspond to the types indicated by the layout information, in the size and the positional arrangement indicated by the layout information. In other words, the display controlling unit 26c displays, on the localizer screen, the reference cross-sectional images corresponding to the types acquired by the imaging scans performed according to the protocols including and following the protocol 85 that is set immediately subsequent to the cross-section detecting protocol 86 set between the protocol 84 and the protocol 85.

Consequently, the MRI apparatus according to the second modification example the second embodiment displays, on the localizer screen, only such reference cross-sectional images that are acquired by the imaging scans performed according to the protocols that are to be processed from now on. Accordingly, the MRI apparatus according to the second modification example of the second embodiment makes it possible for the user to perform the localizer process on the reference cross-sectional images even more easily.

The magnetic resonance imaging apparatus according to at least one of the embodiments described above makes it possible for the user to easily perform the localizer process on the cross-sectional images.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus, comprising: processing circuitry configured to
   acquire layout information, which defines a layout of cross-sectional images on a localizer screen, the localizer screen being displayed prior to a main image taking process,
   detect cross-sectional positions of the cross-sectional images from magnetic resonance (MR) data, anatomical characteristics which define types of the cross-sectional images being different among the cross-sectional positions, and
   generate the localizer screen according to the layout information, the localizer screen including the cross-sectional images generated based on the detected cross-sectional positions, wherein,
   the processing circuitry is configured to receive the types of the cross-sectional images while causing a display to display a correlation diagram indicating relationships among the types of the cross-sectional images and store the layout information defining the layout of the cross-sectional images corresponding to the received types of the cross-sectional images into a memory, the correlation diagram including a plurality of reference cross-sectional images and not including the cross-sectional images generated based on the detected cross-sectional positions, and
   the processing circuitry is configured to receive the types of the cross-sectional images via a receiving screen including the correlation diagram, the receiving screen being displayed prior to the main image taking process.

2. The apparatus according to claim 1, wherein a plurality of pieces of the layout information is defined according to a type of an image taking process included in an examination protocol.

3. The apparatus according to claim 1, wherein, while further causing the display to display a procedure for setting the plurality of reference cross-sectional images, the processing circuitry is further configured to receive the type of cross-sectional images.

4. A magnetic resonance imaging apparatus, comprising: processing circuitry configured to
   detect cross-sectional positions of cross-sectional images from magnetic resonance (MR) data,
   generate layout information defining a layout on a localizer screen according to an examination protocol, the localizer screen being displayed prior to a main image taking process, and
   generate the localizer screen according to the layout information, the localizer screen including all or a part of a plurality of cross-sectional images generated based on the plurality of cross-sectional positions,
   wherein, when a plurality of image taking processes are performed according to a plurality of protocols included in the examination protocol, the plurality of protocols comprising a first protocol, a second protocol, and a third protocol, and when the third protocol defining an image taking condition for performing a predetermined process is set between the first protocol and the second protocol after an image taking process of the first protocol is completed and before an image taking process of the second protocol begins, the processing circuitry is further configured to generate the layout information defining the layout including types of the cross-sectional images acquired by image taking processes performed according to the second protocol and protocols subsequent to the second protocol, and generate the localizer screen according to the layout information.

5. The apparatus according to claim 4, wherein the processing circuitry is further configured to generate the layout information defining the layout including a type of the cross-sectional images acquired by the plurality of image taking processes and generate the localizer screen according to the layout information.

6. The apparatus according to claim 4, wherein the processing circuitry is further configured to generate the layout information defining the layout including a type of the cross-sectional images acquired by a not-yet-performed image taking process, and generate the localizer screen according to the layout information.

7. The apparatus according to claim 1, further comprising the memory to store the layout information.

8. A magnetic resonance imaging apparatus, comprising:
   a magnetic resonance imaging (MRI) system configured to acquire a magnetic resonance (MR) image;
   a processor; and
   a memory that stores processor-executable instructions that, when executed by the processor, cause the processor to:
   acquire layout information which defines a layout of cross-sectional images on a localizer screen, the localizer screen being displayed prior to a main image taking process,
   detect cross-sectional positions of the cross-sectional images from MR data, anatomical characteristics which define types of the cross-sectional images being different among the cross-sectional positions, and
   generate the localizer screen according to the information, the localizer screen including the cross-sectional images generated based on the detected cross-sectional positions, wherein the memory further stores processor-executable instructions that, when executed by the processor, cause the processor to receive the types of the cross-sectional images while causing a display to display a correlation diagram indicating relationships among the types of the cross-sectional images, the memory further stores the layout information defining the layout of the cross-sectional images corresponding to the received types of the cross-sectional images, the correlation diagram including a plurality of reference cross-sectional images and not including the cross-sectional images generated based on the detected cross-sectional positions, and the memory further stores processor-executable instructions that, when executed by the processor, cause the processor to receive the types of the cross-sectional images via a receiving screen including the correlation diagram, the receiving screen being displayed prior to the main image taking process.

9. The apparatus according to claim 8, further comprising the display to display the localizer screen.

10. A medical image processing method, comprising:
acquiring layout information which defines a layout of cross-sectional images on a localizer screen, the localizer screen being displayed prior to a main image taking process, detecting cross-sectional positions of the cross-sectional images from magnetic resonance (MR) data, anatomical characteristics which define types of the cross-sectional images being different among the types of the cross-sectional positions, and generating the localizer screen according to the layout information, the localizer screen including the cross-sectional images generated based on the detected cross-sectional positions, wherein the medical image processing method further includes receiving the types of the cross-sectional images, while causing a display to display a correlation diagram indicating relationships among the types of cross-sectional images and storing the layout information defining the layout including the received types of the cross-sectional images into a memory, the correlation diagram including a plurality of reference cross-sectional images and not including the cross-sectional images generated based on the detected cross-sectional positions, and receiving the types of the cross-sectional images via a receiving screen including the correlation diagram, the receiving screen being displayed prior to the main image taking process.

11. The magnetic resonance imaging apparatus according to claim 1, wherein the processing circuitry is further configured to cause the display to display the correlation diagram of the cross-sectional images and receive, from a user, a selection of a cross-sectional image among the correlation diagram, to generate the layout information.

12. The magnetic resonance imaging apparatus according to claim 1, wherein the processing circuitry is configured to receive the types of the cross-sectional images via the displayed correlation diagram.

* * * * *